United States Patent
Maekawa et al.

(10) Patent No.: US 7,189,810 B2
(45) Date of Patent: Mar. 13, 2007

(54) POLYPEPTIDES, USE THEREOF AND PROCESS FOR PRODUCING THE SAME

(75) Inventors: Takami Maekawa, Kawasaki (JP);
Hisao Fukuda, Kawasaki (JP);
Fumihiko Yokoya, Kawasaki (JP);
Tomohisa Okutsu, Kawasaki (JP);
Yoshiyuki Takahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 334 days.

(21) Appl. No.: 10/327,995

(22) Filed: Dec. 26, 2002

(65) Prior Publication Data

US 2003/0187185 A1  Oct. 2, 2003

Related U.S. Application Data

(63) Continuation of application No. PCT/JP01/05415, filed on Jun. 25, 2001.

(30) Foreign Application Priority Data

Jun. 26, 2000   (JP) .............................. 2000-191379

(51) Int. Cl.
*C07K 2/00*   (2006.01)
*G01N 33/53*  (2006.01)
*C12P 21/08*  (2006.01)

(52) U.S. Cl. ............... 530/350; 424/189.1; 424/389.1; 424/391.1; 435/7.1; 435/69.1; 435/975

(58) Field of Classification Search ............... 530/350; 424/189.1; 435/975, 69.1, 5
See application file for complete search history.

(56) References Cited

U.S. PATENT DOCUMENTS 5,474,905 A * 12/1995 Tai et al. .................... 435/7.34

2004/0024181 A1 * 2/2004 Gangolli et al. ............ 530/350

FOREIGN PATENT DOCUMENTS

WO   WO 92/18532   10/1992
WO   WO 00/58473   10/2000

OTHER PUBLICATIONS

Strausberg et al. PNAS Dec. 24, 2002, vol. 99, No. 26, pp. 16899-16903.*
Strausberg et al. P.N.A.S. 2002, vol. 99, No. 26, pp. 16899-16903.*
NCBI.,Acc. BC014187.*
Borud et al. Molecular endocrinology 2003, vol. 17, No. 11, pp. 2303-2319.*
NCBI AY072704.*
I. Ozaki, et al., "Differential expression of laminin receptors in human hepatocellular carcinoma", GUT, vol. 43, No. 6, XP-002305542, Dec. 1998, pp. 837-842.
T. Yamashita, et al., *Biochemical and Biophysical Research Communications*, vol. 269, pp. 110-116 (2000).
Eui-Cheol Shin, et al., "Expression of Fas-Related Genes in Human Hepatocellular Carcinomas", Cancer Letters, vol. 134, No. 2, XP-002305541, Dec. 25, 1998, pp. 155-162.
Watson, et al., "Translational Controls: Fact, Not Fantasy and Translational Control of Hemoglobin Synthesis by Heme", Molecular Biology of the Gene, 1987, pp. 729-730.

* cited by examiner

*Primary Examiner*—Bruce Campell
*Assistant Examiner*—Bao Qun Li
(74) *Attorney, Agent, or Firm*—Oblon, Spivak, McClelland, Maier & Neustadt, P.C.

(57) ABSTRACT

An isolated polypeptide comprises the amino acid sequence of SEQ ID NO: 11, wherein the expression of said polypeptide is significant lower specifically in human livers with hepatitis compared with that in human health livers. The detection of said polypeptide expression in human liver can be used as a diagnosis for human hepatitis.

11 Claims, 7 Drawing Sheets

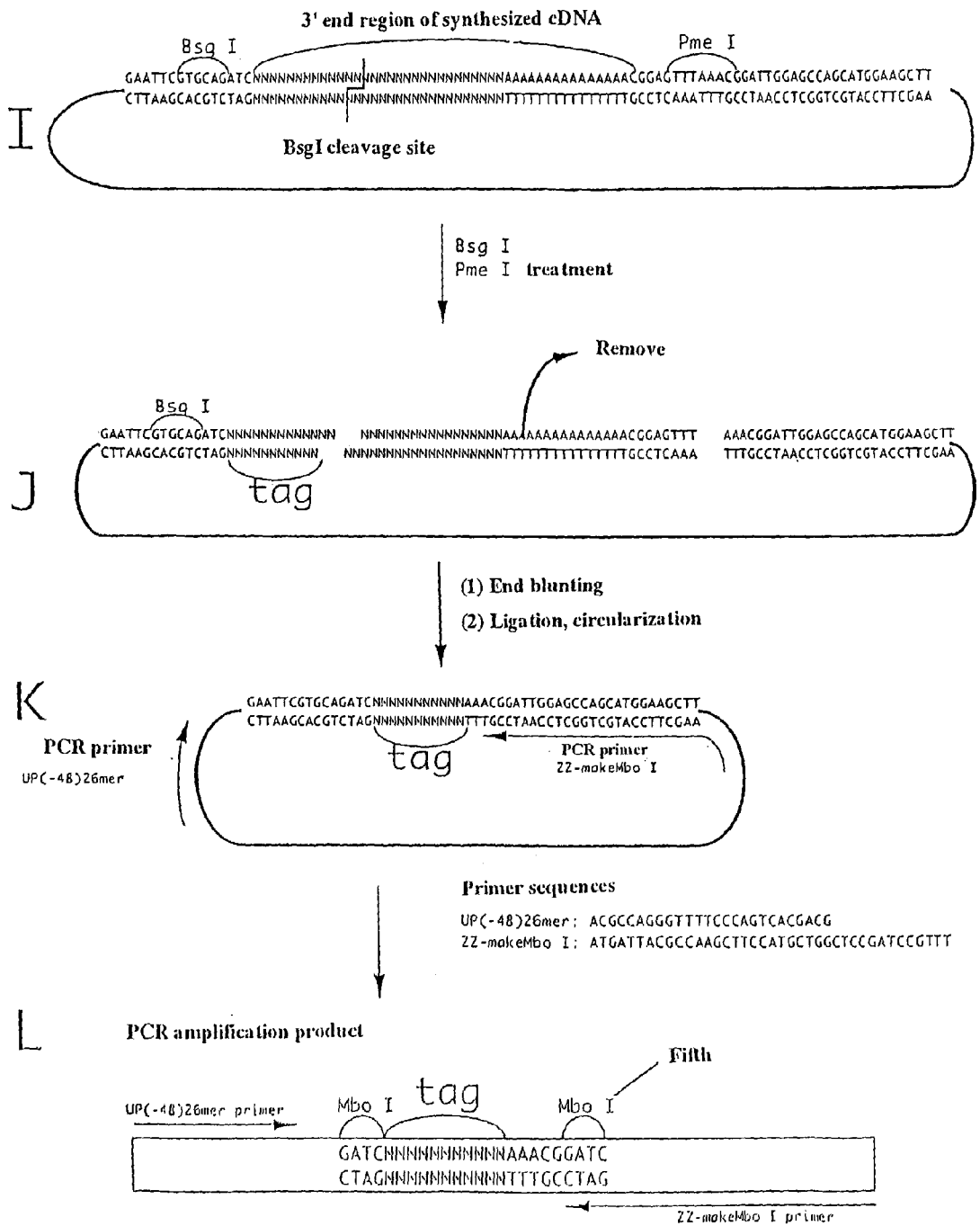

US 7,189,810 B2

POLYPEPTIDES, USE THEREOF AND PROCESS FOR PRODUCING THE SAME

CONTINUING APPLICATION DATA

This application is a Continuation of International Application No. PCT/JP01/05415, hereby incorporated by reference as if fully set forth herein.

BACKGROUND OF THE INVENTION

1. Field of the Invention

The present invention relates to polypeptides having a production level specifically lowered in human livers having inflammation ("diseased livers") as well as their preparation methods and uses, i.e., methods for diagnosing hepatitis by determining the production level of the polypeptides in the liver and diagnostic kits for diagnosing hepatitis by determining the production level of the polypeptides in the liver.

2. Description of the Background

Hepatitis shows significantly varying clinical pictures or histopathological features depending on the cause, severity and stage. Thus, diagnosis/treatment of hepatitis requires a comprehensive judgment based on clinical pictures, histopathological observation and hepatic function tests, etc.

A novel diagnostic means for such hepatitis would be effective for improving a basic understanding of hepatitis or for diagnosis/treatment of hepatitis.

Accordingly, there remains a need to provide novel diagnostic means for hepatitis.

SUMMARY OF THE INVENTION

It is an object of the present invention to provide a novel diagnostic means for hepatitis.

The object described above was achieved by finding polypeptides having a production level specifically lowered in diseased livers and further studies based on this finding.

Accordingly, an aspect of the present invention is a polypeptide having the amino acid sequence shown in SEQ ID NO: 11 or SEQ ID NO: 12 and having a production level specifically lowered in human diseased livers.

Another aspect of the present invention is a diagnostic method for hepatitis comprising determining the production level of the polypeptide in the liver. A specific embodiment of this diagnostic method comprises determining the production level of mRNA encoding the polypeptide (or its cDNA) in the liver as the production level of the polypeptide in the liver. Another specific embodiment of this diagnostic method comprises using an antibody against the polypeptide.

Further aspects of the present invention are diagnostic kits for diagnosing hepatitis by determining the production level of the polypeptide in the liver, the kits comprising a container receiving the polypeptide, a container receiving an antibody against the polypeptide, and a container receiving an oligonucleotide specifically hybridizing to an mRNA encoding the polypeptide (or its cDNA), respectively.

An aspect of the present invention is a DNA containing a gene encoding the polypeptide.

Another aspect of the present invention is a method for preparing the polypeptide comprising culturing a host cell transformed with the DNA.

A more complete appreciation of the invention and many of the attendant advantages thereof will be readily obtained as the same becomes better understood by reference to the following Figures in conjunction with the detailed description below.

BRIEF DESCRIPTION OF THE DRAWINGS

FIG. 2D is a (partial) schematic view showing the process for preparing and counting tags representing mRNA. In panel I, the top polynucleotide appearing as 5' to 3' is the sequence of SEQ ID NO: 37 and the bottom polynucleotide appearing as 3' to 5' is the sequence of SEQ ID NO: 38. In panel J, the top polynucleotides appearing as 5' to 3' sequences are represented as the sequences of SEQ ID NO: 39, SEQ ID NO: 40, and SEQ ID NO: 41 (from left to right) and the bottom polynucleotides appearing as 3' to 5' sequences are represented as the sequences of SEQ ID NO: 42, SEQ ID NO: 43, and SEQ ID NO: 44 (from left to right). In panel K, the top polynucleotide appearing as 5' to 3' is the sequence of SEQ ID NO: 45 and the bottom polynucleotide appearing as 3' to 5' is the sequence of SEQ ID NO: 46. Alongside the arrow between panels K and L, the primer sequence designated as UP(−48)26mer is the sequence represented by SEQ ID NO: 2 and the primer sequence designated as ZZ-makeMbo I is the sequence represented by SEQ ID NO: 3. In panel L, the top polynucleotide appearing as 5' to 3' is the sequence of SEQ ID NO: 47 and the bottom polynucleotide appearing as 3' to 5' is the sequence of SEQ ID NO: 48.

DETAILED DESCRIPTION OF THE INVENTION

Figure 1:
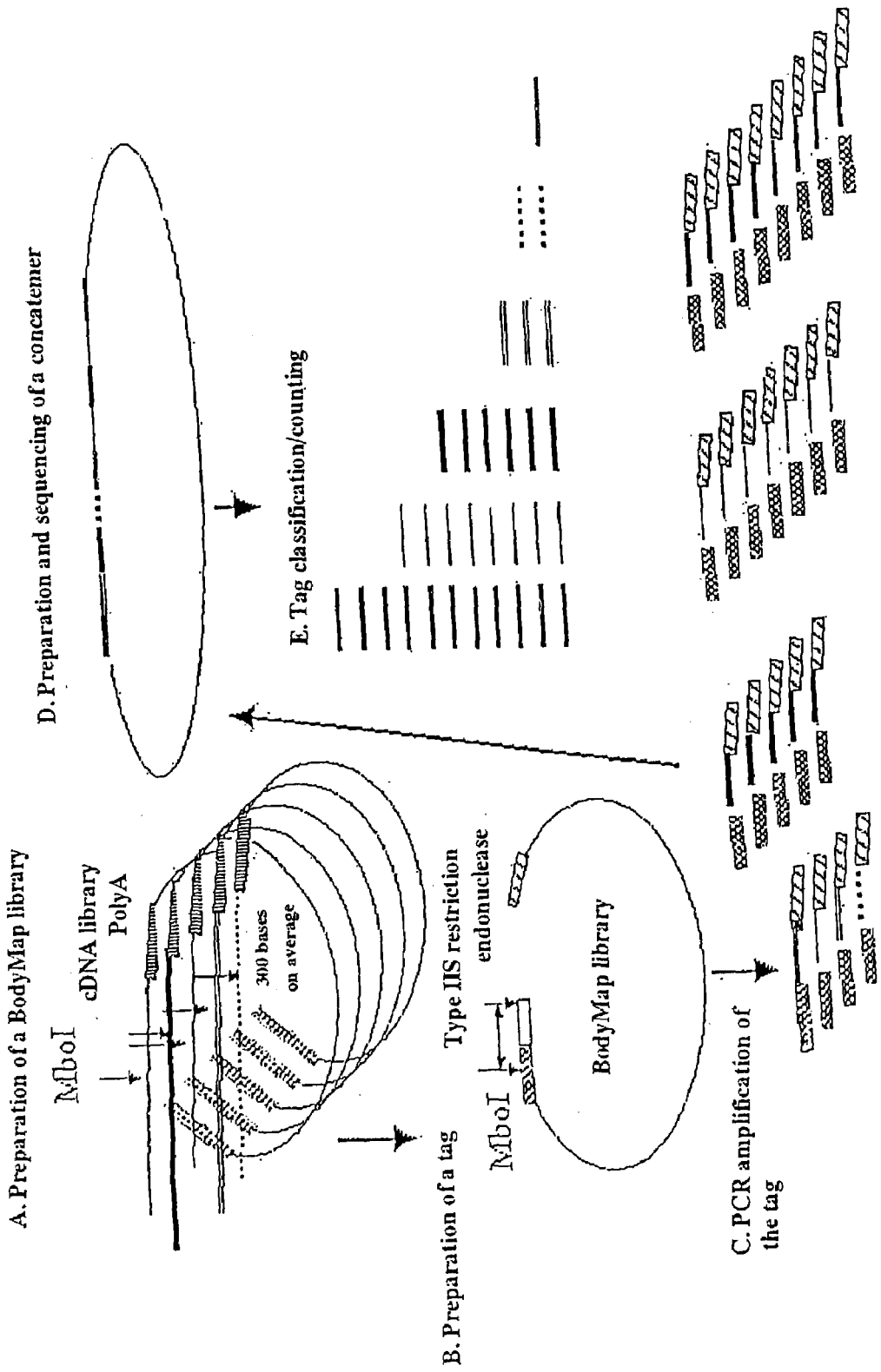
FIG. 1 is a schematic view showing a summarized process for preparing and counting tags representing mRNA.

As used herein, the "hepatitis" means to include any hepatitis irrespective of the cause. Namely, it includes infectious hepatitis caused by virus or other infectious agents, hepatitis induced by drugs such as alcohol or other drugs, and autoimmune hepatitis induced by autoimmune mechanism. Hepatitis viruses are well known as viruses causing hepatitis, in addition to which infection with Epstein-Barr virus or cytomegalovirus may also develop hepatitis. Infections with other infectious agents than viruses such as *Salmonella typhi*, Brucella, *Entamoeba dysenteriae*, pathogenic leptospire (Weil's disease) may also develop hepatitis. Many hepatitis viruses have been isolated such as type A, type B and type C hepatitis viruses and non-A non-B non-C hepatitis viruses, and the presence of many other viruses is predicted.

Hepatitis is classified by the severity or stage into acute hepatitis, fulminant hepatitis, subacute hepatitis, persistent hepatitis, chronic hepatitis, etc. As used herein, the "hepatitis" means to include any hepatitis of these classes.

As used herein, the "production level" means the amount of a polypeptide of the present invention accumulated in liver tissues or the amount of mRNA encoding a polypeptide of the present invention (or its cDNA) at a point of time. Thus, the average of the amounts of a polypeptide of the present invention accumulated in liver tissues or the amounts of mRNA encoding a polypeptide of the present invention (or its cDNA) at two or more different points of time is also included in the definition of the "production level" as used herein.

The polypeptide of the present invention has a production level specifically lowered in diseased livers as described in the examples below. Thus, the presence of hepatitis can be diagnosed by determining the production level of the polypeptide in the liver.

The production level of the polypeptide in the liver is closely and specifically related to hepatitis, suggesting that diseases associated with an increase or decrease of the activity of the polypeptide can be treated by controlling the activity of the polypeptide in the liver (i.e., increasing or decreasing the amount of the polypeptide or enhancing or suppressing the activity of the polypeptide). In order to increase the amount of the polypeptide, the polypeptide can be externally supplied or a means for enhancing the expression of the gene encoding the polypeptide can be taken. In order to decrease the amount of the polypeptide, the expression of the gene encoding the polypeptide can be suppressed. The activity of the polypeptide can be suppressed by supplying a compound that inhibits the activity of the polypeptide. A possible means for enhancing/suppressing the expression of the gene encoding the polypeptide is to administer a sense gene or an antisense gene. It is also possible to administer an antibody against the polypeptide, e.g., a humanized antibody. The relation between the production level of the polypeptide in the liver and pathology can be clarified by allowing the gene encoding the polypeptide to be specifically expressed in the liver (e.g., by the use of the albumin promoter/enhancer described in Pinkert, C. A., et al., Genes Dev., 1, 268–276 (1987), hereby incorporated by reference as if fully set forth herein).

Polypeptides of the present invention have the amino acid sequence shown in SEQ ID NO: 11 or SEQ ID NO: 12.

Analysis of the amino acid sequence of SEQ ID NO: 11 or SEQ ID NO: 12 showed that a zinc finger motif of $C_2H_2$ class (having 2 cysteine molecules and 2 histidine molecules) recurs five times at the C-terminus. The zinc finger motif is a steric structure characteristic of a DNA-binding domain of a DNA-binding protein, and proteins having a zinc finger domain are known to have transcription factor activity of RNA polymerase III (TFIIIA). Therefore, polypeptides of the present invention are thought to have transcription factor activity.

Intracellular localization of a polypeptide having the amino acid sequence shown in SEQ ID NO: 11 was verified by designing an expression vector expressing a fused peptide having a hemagglutinin-tag (HA-tag) at the N-terminus of the polypeptide and observing cells transfected with the vector under a fluorescent microscope.

The result showed that the polypeptide is localized at the nucleus, especially at the nuclear body-like structure. The nuclear body is a place where DNA is transcribed into RNA very actively, suggesting that the polypeptide of SEQ ID NO: 11 having a zinc finger motif should be a transcription factor that binds to DNA under active transcription to regulate the transcription.

The expression levels of the genes encoding SEQ ID NO: 11 and SEQ ID NO: 12 in the liver of a plurality of hepatitis patients were examined using a TaqMan kit from PE Biosystems to show that the genes were weakly expressed at the stage of severe condition of hepatitis while the expression level increased after recovery.

The production level of the polypeptide of the present invention in the liver decreases only when it has hepatitis (irrespective of other factors, i.e., "specifically"), as described above. Thus, the diagnosis of hepatitis according to the present invention can be performed by determining the production level of the polypeptide in a liver and comparing it with the production level of the polypeptide in a liver not having hepatitis. The liver is diagnosed as having hepatitis or not, depending on whether the measurement result of the production level of the polypeptide in the liver is lower than or comparable to the production level of the polypeptide in the liver not having hepatitis.

In order to determine the production level of the polypeptide of the present invention in the liver, liver biopsies are used as samples. Methods for collecting biopsies are well known. Pretreatments of collected biopsies before analysis depend on the subsequent analytic method of the polypeptide, as well known to those skilled in the art.

The production level of the polypeptide of the present invention in the liver may be determined by taking advantage of the structural characteristics of the polypeptide, but it is preferably determined by the following two methods.

A first method uses an antibody.

Suitable antibodies may be polyclonal, but especially preferred are monoclonal antibodies. Both monoclonal and polyclonal antibodies may be used in one diagnostic method (or one diagnostic kit). Antibodies here also include humanized antibodies and antibody fragments retaining the ability to specifically bind the antigen.

Antibodies against polypeptides of the present invention can be obtained by ordinary methods for obtaining antibodies against proteins. That is, goats, rabbits or mice or the like may be immunized with a polypeptide of the present invention to give an antiserum or spleen B cells for obtaining monoclonal antibodies. Methods for preparing humanized antibodies or antibody fragments are also well known.

Antigens (i.e., polypeptides of the present invention) used to obtain the antibodies are preferably highly purified. Polypeptides of the present invention used as antigens may be a polypeptide having all the amino acids of the amino acid sequence of SEQ ID NO: 11 or SEQ ID NO: 12 or a part thereof, especially a part thereof containing an antigenic determinant (epitope). Fused proteins of a polypeptide of the present invention fused to another polypeptide may also be used as antigens.

Various methods for determining the amount of a protein using an antibody (immunoassays) have been proposed, and any of them can be applied to the measurement of the production level of the polypeptide.

Briefly, a preferred method for increasing the accuracy of measurement is to label the antibody or antigen (a polypeptide of the present invention), as well known. If the antigen is labeled (competitive assay), the labeled antigen and the antigen in a sample (a polypeptide of the present invention) compete for the reaction with their antibodies. Thus, the amount of the antigen in the sample can be known by measuring the amount of the reaction product between the antibody and the labeled antigen (labeled antigen-antibody reaction product). If the antibody is labeled (non-competitive assay), the amount of the antigen in a sample can be known from the labeled antigen-antibody reaction product resulting from the reaction between the antigen in the sample and the labeled antibody.

Typical examples of suitable labels include enzymes (involved in color development reaction), radioisotopes, stained colloids (gold colloid, selenium colloid, etc.), fluorescent and chemiluminescent compounds (acridinium salts, etc.). The antibody or antigen may not be always labeled, but a compound specifically reacting with the antibody or antigen [e.g., an antibody against a mouse antibody (i.e., an antibody against a polypeptide of the present invention)] may also be labeled.

The antigen-antibody reaction product can be separated from unreacted antigen and/or antibody by the homogeneous reaction method involving an antigen-antibody reaction in a homogeneous system or the heterogeneous reaction method involving immobilizing the antibody to a solid phase when the antigen is to be assayed. When the antigen is to be assayed, the heterogeneous reaction method using a labeled antibody is called sandwich method.

Widely used solid phases in the heterogeneous reaction system include chromatographic carriers (carriers with capillaries) and microbeads of various materials. Container walls such as wells may also be used as solid phases. As for immobilized antibodies, antibodies may not always be immobilized but a compound specifically binding an antibody against a polypeptide of the present invention (e.g., an antibody against a mouse antibody) or a compound specifically binding a conjugate of a polypeptide of the present invention with another compound (e.g., biotin or avidin) may be immobilized to a solid phase.

According to a specific method for determining the amount of a polypeptide of the present invention, a labeled antibody as described above can also be used to measure the amount of the polypeptide of the present invention in an experimental animal tissue manipulated to produce the human polypeptide of the present invention or in a human biopsy.

A second method for determining the production level of a polypeptide of the present invention in the liver is based on the positive correlation between the production level of mRNA encoding the polypeptide of the present invention and the production level of the polypeptide. That is, the second method comprises determining the production level of mRNA encoding a polypeptide of the present invention as the production level of the polypeptide of the present invention.

The determination of the production level of the mRNA involves measuring the amount of the mRNA or measuring the amount of cDNA of the mRNA, A typical method for measuring this mRNA or cDNA comprises using an oligonucleotide specifically hybridizing to the mRNA or cDNA.

A preferable such oligonucleotide can be readily selected on the basis of the amino acid sequence (SEQ ID NO: 11 and SEQ ID NO: 12) of polypeptides of the present invention disclosed herein. That is, a nucleotide sequence specific to the mRNA or cDNA in the mRNA or cDNA can be found without difficulty by using information from data banks, if desired. Furthermore, an oligonucleotide having a nucleotide length as close as possible to the total nucleotide length of the mRNA or cDNA can be used. In addition, this oligonucleotide may not have a complementary nucleotide sequence completely homologous to the specific nucleotide sequence in the mRNA or cDNA. Even an oligonucleotide not having a completely homologous complementary nucleotide sequence can hybridize to the mRNA or cDNA by appropriately selecting hybridization conditions (stringency). It is well known that stringency can be especially controlled by the reaction temperature and the salt concentration of the reaction solution.

The oligonucleotide has a length of 10 bases or more, preferably 15 bases or more (e.g., 25, 30, 40).

This oligonucleotide is typically labeled for assaying its hybrid to the mRNA or cDNA. The detection sensitivity of the mRNA or cDNA can be sometimes improved by using two or more labeled oligonucleotides hybridizing to different sites of the mRNA or cDNA or hybridizing to concomitant nucleic acids at different degrees. In this case, two or more different labels are preferably used.

Many methods for separating the oligonucleotide portions having hybridized and not to the mRNA or cDNA are also known. In the present invention, any of these methods can be applied.

The assay of the mRNA or cDNA can also be combined with a nucleic acid amplification method such as PCR. In this case, the amount of the mRNA or cDNA is calculated on the basis of the amplification speed of the amplification product.

The amplification speed can be determined by measuring the increasing speed of the fluorescence amount in a PCR reaction using an oligonucleotide (DNA) probe designed to emit fluorescence as the PCR reaction proceeds. Alternatively, a distinct synthetic DNA from that for other cDNAs (with the molecular weight or nucleotide sequence being distinct from those of the synthetic DNA added to the other cDNAs) can be added to the cDNA of the mRNA (the nucleotide sequence of the cDNA encoding this polypeptide is disclosed herein) and PCR primers for this synthetic DNA can be used for PCR amplification to determine the amount of the PCR amplification product on the basis of the difference of the molecular weight or nucleotide sequence of the synthetic DNA.

A specific method for assaying the mRNA to determine the amount of a polypeptide of the present invention is a northern blotting method using a labeled oligopeptide as described above. According to another specific method for assaying the mRNA to determine the amount of a polypeptide of the present invention, a labeled oligopeptide as described above can be used to determine the distribution or amount in an experimental animal tissue manipulated to produce mRNA encoding the human polypeptide of the present invention or in a human tissue biopsy.

Polypeptides of the present invention may be both or either one of a polypeptide having the amino acid sequence of SEQ ID NO: 11 and a polypeptide having the amino acid sequence of SEQ ID NO: 12, but this will be no obstacle to determining the production level of the polypeptide in the liver using an antibody against the polypeptide or an oligopeptide specifically hybridizing to mRNA encoding the polypeptide or its cDNA. This is because the amino acid sequence of SEQ ID NO: 11 and the amino acid sequence of SEQ ID NO: 12 have a common nucleotide sequence region and a common amino acid sequence region at the C-terminus (the amino acid sequence of SEQ ID NO: 12 contains a further amino acid sequence added to the N-terminus of the amino acid sequence of SEQ ID NO: 11). Thus, the antibody or oligopeptide used to determine the production level of the polypeptide in the liver can be the same whether the polypeptide of the present invention is both or either one of a polypeptide having the amino acid sequence of SEQ ID NO: 11 and a polypeptide having the amino acid sequence of SEQ ID NO: 12.

As used herein, the "diagnostic kit" comprises a container receiving at least one reagent used in a diagnostic method of the present invention. Therefore, a container receiving a diagnostic agent used for a diagnostic method of the present invention in a laboratory is also included in the diagnostic kit of the present invention.

In a first case, the diagnostic agent received in the container in the diagnostic kit of the present invention may be a polypeptide of the present invention. In this case, the polypeptide of the present invention will be used as a control reagent (positive control). If desired, the polypeptide may be immobilized to a solid phase or labeled. In a second case, the diagnostic agent may be an antibody that specifically reacts with a polypeptide of the present invention. The antibody may be labeled or not. The antibody may be immobilized or not to a solid phase. In a third case, the diagnostic agent may be an oligonucleotide that specifically hybridizes to an mRNA encoding a polypeptide of the present invention or its cDNA. This oligonucleotide may be immobilized or not to a solid phase. It may be labeled or not. In a fourth case, the diagnostic agent may be the cDNA of an mRNA encoding a polypeptide of the present invention. The cDNA is used as a positive control to determine the amount of cDNA by measuring the amplification speed in PCR amplification or to determine the amount of cDNA by hybridization with a labeled oligonucleotide.

In addition to the diagnostic agent, the diagnostic kit of the present invention may comprise a container receiving other reagents necessary for a diagnostic method of the present invention. Those other reagents widely vary such as color developing reagents in immunoassays, buffers, necessary reagents for separating the oligonucleotide bound to mRNA if it should be separated, necessary reagents for separating the double strand of a hybrid between mRNA (or cDNA) and an oligonucleotide if it should be separated, necessary reagents for PCR amplification, etc.

The DNA containing a gene encoding a polypeptide of the present invention comprises a DNA encoding the polypeptide of the present invention alone or in combination with other DNA fragments. Such other DNA fragments include vector DNA (including expression and cloning vectors). They also include expression regulating regions such as transcription regulating elements added to the 5' end of the gene or untranslated regions added to the 3' end. They also include a DNA encoding another protein or protein fragment added to the 5' end, for example. (In this case, a fused protein is produced. Such a fused protein is also included in polypeptides of the present invention. Such a fused protein included in polypeptides of the present invention is used to prepare an antibody against a polypeptide of the present invention, for example.)

A gene encoding a polypeptide of the present invention can be readily obtained on the basis of information such as the amino acid sequences of polypeptides encoded thereby (SEQ ID NO: 11 and SEQ ID NO: 12) disclosed herein or the nucleotide sequences of the coding regions (SEQ ID NO: 10 and SEQ ID NO: 17) disclosed herein. A necessary method for this is described in T. Maniatis et al., "Molecular Cloning: A Laboratory Manual", Cold Spring Harbor Laboratory (1982), hereby incorporated by reference as if fully set forth herein.

A typical method for this is briefly described below. PCR primers are prepared on the basis of the nucleotide sequences corresponding to the amino acid sequences of polypeptides of the present invention described herein to give PCR product DNA from polyA$^+$ mRNA in human liver (normally after conversion into a cDNA library), and the resulting PCR product DNA is cloned (using a cDNA cloning vector such as pIBI24/25 (IBI, New Haven, Conn.), M13 mp 18/19, pGEM4, pGEM3, pGEM7Z and pSP72), and then the cloned PCR product DNA is characterized by sequencing and restriction endonuclease restriction mapping. When the nucleotide sequences of the cloned and characterized PCR product DNA fragments have overlapping nucleotide sequence regions (overlapping clones), these fragments are assembled to generate a contig with the overlapping nucleotide sequence regions being aligned.

According to another typical method, a cDNA library is prepared from mRNA in human liver (or may be commercially available), and a probe is prepared on the basis of the amino acid sequence of a polypeptide of the present invention disclosed herein (SEQ ID NO: 11 or SEQ ID NO: 12) or the nucleotide sequence corresponding to the amino acid sequence (SEQ ID NO: 10 or SEQ ID NO: 17) and the probe is used to select the target cDNA from the cDNA library.

Verification of thus obtained DNA as DNA of the present invention (encoding a polypeptide of the present invention) is performed by identifying the translation start codon and the translation stop codon in the nucleotide sequence of the DNA to identify the coding region. Alternatively, it may be possible to directly read from the nucleotide sequence whether or not thus obtained DNA encodes the amino acid sequence of a polypeptide of the present invention. In any way, it may be confirmed that the DNA obtained has a nucleotide sequence capable of encoding the amino acid sequence of a polypeptide of the present invention.

Methods for transferring DNA of the present invention into a host to give cells having the ability to produce a polypeptide of the present invention are well known. Briefly, suitable host cells include bacteria, yeast, mammalian cells or insect cells, for example. Commercially available mammalian cells include CV-1 (ATCC CL 70), COS-1 (ATCC CRL 1650), COS-7 (ATCC CRL 1651), CHO-K1 (ATCC CCL 61), 3T3 (ATCC CRL 92), NIH/3T3 (ATCC CRL 1658), HeLa (ATCC CCL 2), C127I (ATCC CRL 1616), BS-C1 (ATCC CCL 26) and MRC-5 (ATCC CCL 171).

When a DNA of the present invention is transferred into a host to prepare a polypeptide of the present invention, the DNA of the present invention may exist as an extrachromosomal episome in host cells or may be integrated into a chromosome.

Vectors used for construction of expression vectors should be of course compatible for the host used. They may be shuttle vectors capable of replicating in two hosts (e.g., bacteria—animal cells). Expression vectors often comprise a self-replication start point, a selection marker gene, a promoter sequence, etc. A DNA necessary for an expression vector and having a desired function is inserted into a vector, if it is not contained. Vectors are based on a plasmid, or a virus or phage, or both.

Many of these vectors are commercially available. Examples of commercially available expression vectors functioning in mammalian hosts include PMC1neo (Stratagene), pXT1 (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt ATCC 37199), pRSVneo (ATCC 37198), pSV-dhfr (ATCC 37146), pUT-Cag (ATCC 37460) and λZD35 (ATCC 37565).

Known examples of methods for transferring a DNA of the present invention into host cells include transformation, transfection, bombardment, electroporation, etc.

In order to culture the host in which DNA of the present invention has been introduced to produce a polypeptide of the present invention, the host can be cultured under culture conditions suitable for the growth of the host. If necessary, an expression inducer may be added to the culture medium.

Any special method is not required to isolate/purify the polypeptide of the present invention accumulated in the medium. That is, the polypeptide chain is refolded and purified by column chromatography or other means, if necessary. Affinity purification with an antibody may also be used, if necessary.

The following examples further illustrate the present invention, but are not intended to limit the invention thereto.

EXAMPLES

The following examples illustrate the process by which polypeptides having specifically decreased production in the liver of hepatitis patients were found. This process consists of step [A] and step [B] below.

[A] Preparation of a Gene Expression Profile in the Liver of Hepatitis Patients

A gene expression profile in the liver of hepatitis patients was prepared as follows to identify a gene whose expression is specifically decreased in the liver of hepatitis patients. Preparation of the gene expression profile in human liver comprises preparing tags representing mRNAs, classifying the tags on the basis of their nucleotide sequences and counting the number of tags belonging to each class. Preparation and sequencing of tags comprise the following substeps (FIG. 1).

(A-1) A BodyMap type cDNA library ("BodyMap library" [Gene, 174, 151–158 (1996), hereby incorporated by reference as if fully set forth herein]) is prepared from liver mRNAs of hepatitis and non-hepatitis patients. Preparation of the BodyMap library is summarized as follows. A linearized vector having polyT at one end and an MboI site near the other end is used and polyA of mRNA is attached to polyT of the vector to prepare a cDNA using polyT as a primer. Thus obtained cDNA library is cleaved with MboI and the vector fragment is circularized into a BodyMap library (FIG. 1-A). The MboI site will occur every 300 bases in average in DNA, so that cDNA up to an average of 300 bases upstream of the site corresponding to polyA will remain in the BodyMap library.

(A-2) A tag representing each mRNA is obtained by using the BodyMap library. The BodyMap library is cleaved with type IIS restriction endonuclease (cleaving a certain length of bases apart from the recognition site) and the vector fragment is circularized (FIG. 1-B). The resulting library contains a tag consisting of a specific length of cDNA (normally several tens of bases) determined by the type IIS restriction endonuclease used at the 5' end of the region of an average of 300 bases because the vector preliminarily includes a type IIS restriction endonuclease recognition site adjacent to the MboI site (FIG. 1-B). Then, the tag-containing region is amplified by PCR to give tag-containing DNA fragments (FIG. 1-C).

(A-3) Thus obtained tags are sequenced. Sequencing is performed on a concatemer prepared by concatenating the resulting tag-containing DNA fragments (mixture) (FIG. 1-D).

(A-4) The tags existing in the concatemer are classified into molecular types on the basis of the nucleotide sequence of the concatemer and the number of tags belonging to each class is determined (FIG. 1-E). The number of tags belonging to each class represents the number of members of each mRNA. The increase/decrease of the mRNA in the liver of hepatitis patients as compared with the mRNA in the liver of non-hepatitis patients can be known by determining the number of the mRNA members in the liver of hepatitis patients and the number of the mRNA members in the liver of non-hepatitis patients.

[B] Identification of a Polypeptide Having a Production Level Specifically Decreased in the Liver of Hepatitis Patients Once the tag specifically decreased in the liver of hepatitis patients could be identified by step [A], a gene having the nucleotide sequence of this tag is identified and the polypeptide encoded by the gene is identified.

(B-1) A gene having the nucleotide sequence of the tag is identified. Identification of the gene is performed by searching through tagged ESTs on the basis of the nucleotide sequence of the tag, preparing PCR primers on the basis of the information obtained and using the PCR primers for PCR on a human liver cDNA library.

(B-2) The identified gene is sequenced and its coding region and the amino acid sequence of the polypeptide encoded by the region are determined.

The foregoing experimental procedure is explained in detail below. Experimental methods for the preparation of cDNA libraries, cloning of cDNA, sequencing, etc. can be generally performed by applying standard methods as described in J. Sambrook et al., Molecular Cloning: A Laboratory Manual, second edition, Cold Springer Harbor Laboratory Press (1989), hereby incorporated by reference as if fully set forth herein; Ausubel et al., Current Protocols in Molecular Biology, Wiley-Interscience, New York (1987), hereby incorporated by reference as if fully set forth herein; and Davis et al., Basic Methods in Molecular Biology, Elesevier Science Publishing Co., New York, (1986), hereby incorporated by reference as if fully set forth herein, etc.

[A] Preparation of a Gene Expression Profile in the Liver of Hepatitis Patients (A-1-1) Acquisition of mRNA in the Liver The mRNA was obtained from liver biopsies of hepatitis patients and liver biopsies of these patients after recovery. The resulting gene expression profile was not influenced by the individual difference between hepatitis and non-hepatitis patients because the hepatitis patients and non-hepatitis patients (not having hepatitis) were the same individuals.

Liver tissue biopsies were collected from patients hospitalized by acute hepatitis (Japanese women) at a severe stage immediately after hospitalization (hereinafter referred to as "onset stage") and immediately before leaving the hospital 17 days after hospitalization (hereinafter referred to as "recovery stage"). The collected amount of each biopsy was about 0.8 mm×0.8 mm×7 mm in size. These patients had acute hepatitis type B.

A commercially available mRNA preparing kit (Invitrogen, FastTrack 2.0) was used to prepare mRNA from the collected biopsies (stored at −80° C.) according to the protocol attached to the kit in an amount of about 100 ng each from liver biopsies at onset stage and liver biopsies at recovery stage.

(A-1-2) Preparation of a Vector

A vector was prepared that can be used for the preparation of a cDNA library, a BodyMap library and a tag (FIG. 2B-A, FIG. 2B-C and FIG. 2D-I). This vector contains a restriction site (BstXI in FIG. 2B-A) into which can be inserted a polyT adapter (FIG. 2B-C) having polyT (for inserting single-stranded polyT (having a sufficient length to be attached to polyA of mRNA) to be attached to polyA of mRNA), a first restriction site (used for the preparation of a tag), a second restriction site (used for the preparation of a BodyMap library), a third restriction site (used for the preparation of the BodyMap library and the tag), a fourth and a fifth restriction sites (used for the preparation of the tag) and a type IIS restriction endonuclease cleavage site (BsgI here) (used for the preparation of the tag) in the order shown in FIG. 2B-D, FIG. 2C-E, FIG. 2D-I and FIG. 2D-J.

Figure 2A:
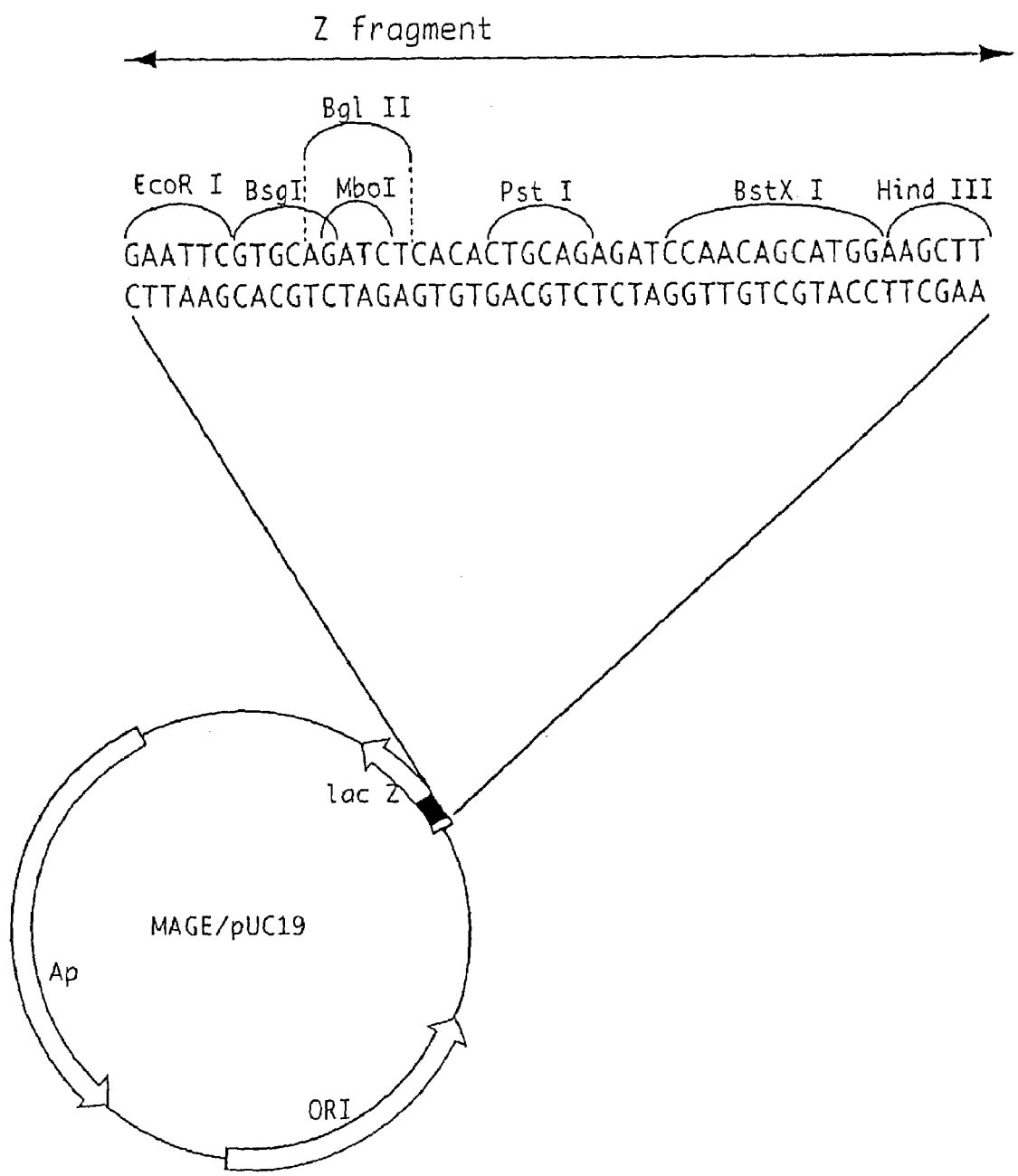
FIG. 2A is a (partial) schematic view showing the process for preparing and counting tags representing mRNA. The top polynucleotide appearing as 5' to 3' is the sequence of SEQ ID NO: 1. The bottom polynucleotide appearing as 3' to 5' is the sequence of SEQ ID NO: 22.
Figure 2B:
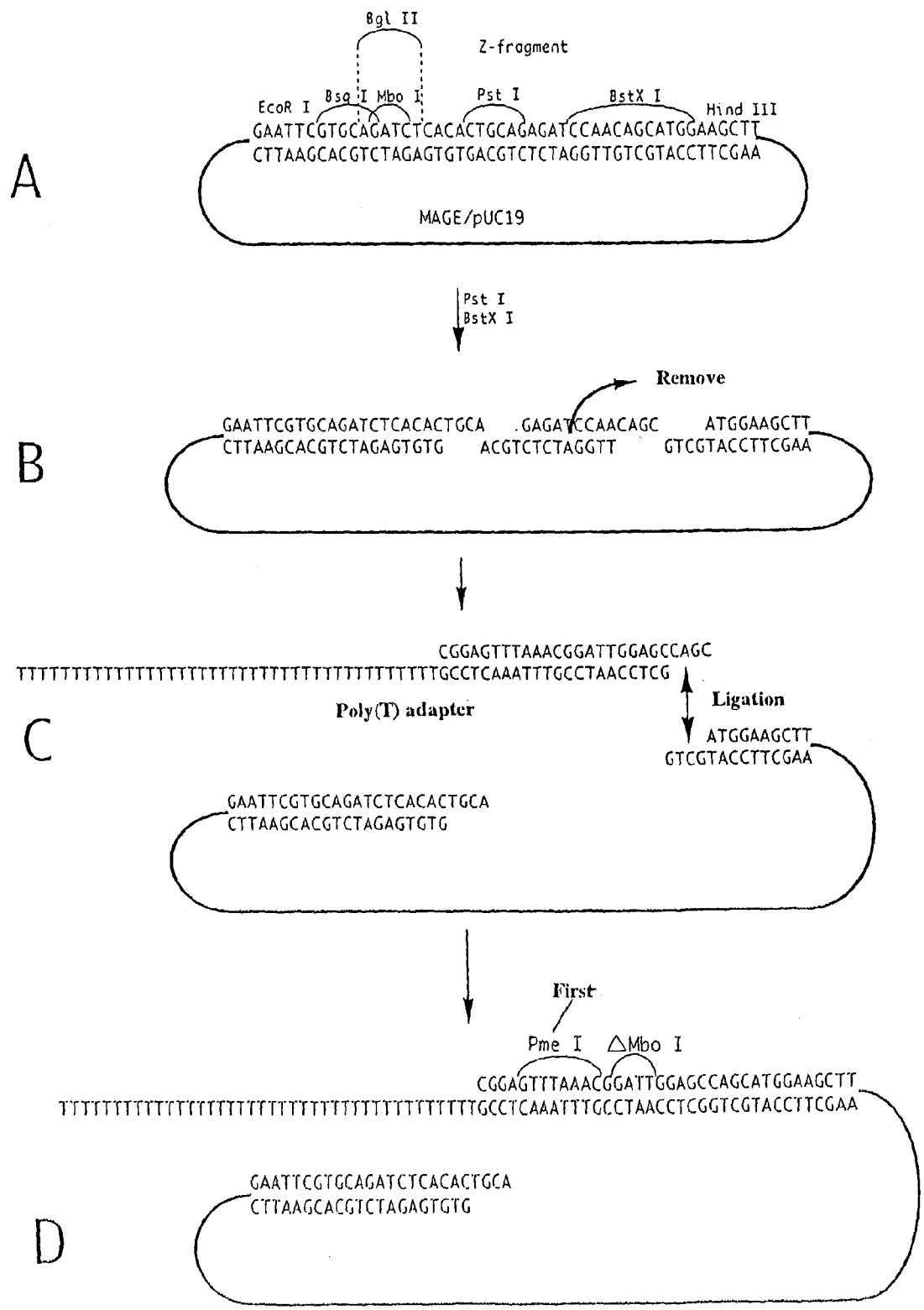
FIG. 2B is a (partial) schematic view showing the process for preparing and counting tags representing mRNA. In panel A, the top polynucleotide appearing as 5' to 3' is the sequence of SEQ ID NO: 1 and the bottom polynucleotide appearing as 3' to 5' is the sequence of SEQ ID NO: 22. In panel B, the top polynucleotides appearing as 5' to 3' sequences are represented as the sequences of SEQ ID NO: 23, SEQ ID NO: 24, and SEQ ID NO: 25 (from left to right) and the bottom polynucleotides appearing as 3' to 5' sequences are represented as the sequences of SEQ ID NO: 26, SEQ ID NO: 27, and SEQ ID NO: 28 (from left to right). In panel C, the top polynucleotides appearing as 5' to 3' sequences are represented as the sequences of SEQ ID NO: 29, SEQ ID NO: 25, and SEQ ID NO: 23 (from top to bottom) and the bottom polynucleotides appearing as 3' to 5' sequences are represented as the sequences of SEQ ID NO: 30, SEQ ID NO: 28, and SEQ ID NO: 26 (from top to bottom). In panel D, the top polynucleotides appearing as 5' to 3' sequences are represented as the sequences of SEQ ID NO: 31 and SEQ ID NO: 23 (from top to bottom) and the bottom polynucleotides appearing as 3' to 5' sequences are represented as the sequences of SEQ ID NO: 32 and SEQ ID NO: 26 (from top to bottom).
Figure 2C:
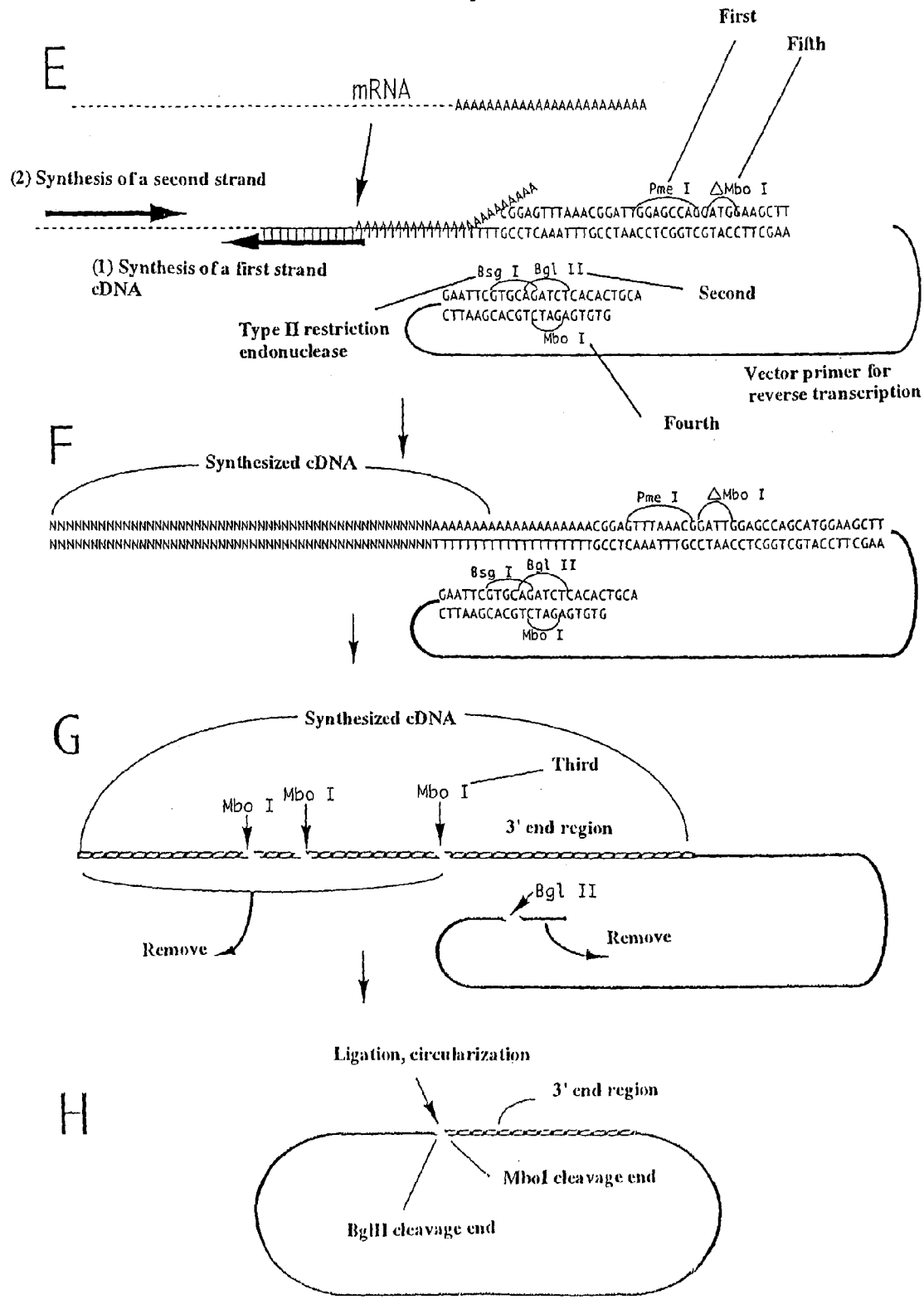
FIG. 2C is a (partial) schematic view showing the process for preparing and counting tags representing mRNA. In panel E, prior to the first arrow, the polynucleotide sequence is an mRNA represented in SEQ ID NO: 33 and is illustrated in the 5' to 3' orientation. In the bottom half of panel E, the top polynucleotides appearing as 5' to 3' sequences are represented as the sequences of SEQ ID NO: 33, SEQ ID NO: 31 and SEQ ID NO: 23 (from top to bottom) and the bottom polynucleotides appearing as 3' to 5' sequences are represented as the sequences of SEQ ID NO: 34 and SEQ ID NO: 26 (from top to bottom). In panel F, the top polynucleotides appearing as 5' to 3' sequences are represented as the sequences of SEQ ID NO: 35 and SEQ ID NO: 23 (from top to bottom) and the bottom polynucleotides appearing as 3' to 5' sequences are represented as the sequences of SEQ ID NO: 36 and SEQ ID NO: 26 (from top to bottom).

This vector was prepared from MAGE/pUC19 (FIG. 2A and FIG. 2B-A) containing a cloning vector pUC19 and a Z fragment (SEQ ID NO: 1) between the EcoRI site and HindIII site thereof. That is, the BstXI site and PstI site in the Z fragment were cleaved and the resulting small fragment was removed (FIG. 2B-B). Then, a polyT adapter was ligated to the BstXI cleavage site (FIG. 2B-D).

(A-1-3) Preparation of cDNA Libraries cDNA libraries of the liver at onset stage and recovery stage were obtained as follows.

Isolation of DNA from reaction solutions was performed in each case by extraction of DNA with phenol/chloroform, then with chloroform from the reaction solution and precipitation with ethanol according to a standard method.

The polyA of mRNA (50 ng) and polyT of the vector (18 ng) described above were annealed to insert mRNA into the vector. Then, the inserted mRNA was performed to reverce transcriptase into cDNA using polyT sequence as a primer (first strand cDNA in FIG. 2C-E).

Figure 2E:
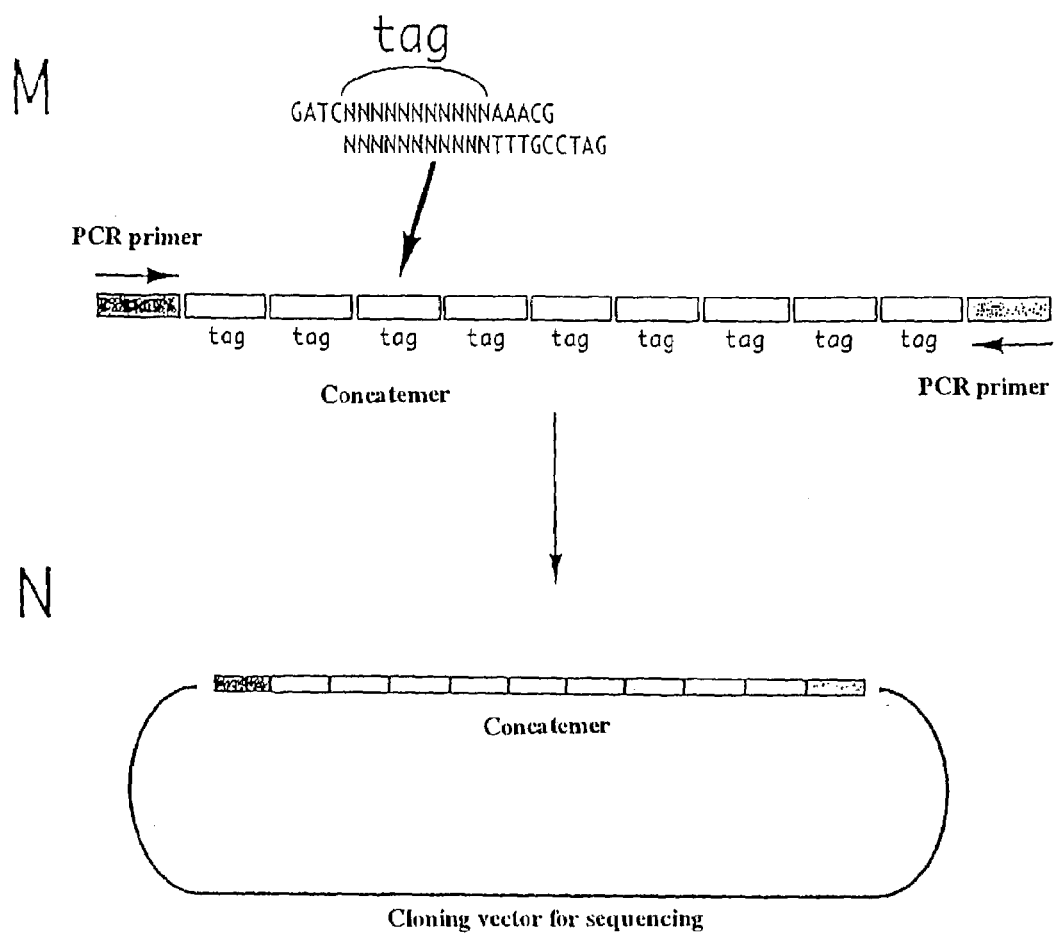
FIG. 2E is a (partial) schematic view showing the process for preparing and counting tags representing mRNA.

Then, THE first strand cDNA was used as a template together with DNA polymerase to synthesize a complementary strand thereto (synthesis of a second strand in FIG. 2C-E), whereby the single-stranded cDNA was converted into a double stranded cDNA (FIG. 2C-E and F).

Reverse transcription (synthesis of a first strand) cDNA Synthesis Kit (Ref. # 6120) from Takara was used.

| | |
|---|---|
| Vector primer | 2.0 μl (containing 18 ng) |
| mRNA (prepared from specimens) | 3.0 μl (containing 50 ng) |
| DEPC (diethyl pyrocarbonate)-treated dH$_2$O | 0.12 μl |
| 5 × first strand synthesizing buffer | 2.2 μl |
| RNase inhibitor (20 U/μl) | 1.1 μl |
| Reverse transferase (RAV-2) | 1.48 μl (containing 2.2 U). |

The first four elements of the above reaction solution composition were premixed, and then heated at 65° C. for 5 minutes and kept on ice. This premix was combined with the remaining three elements, and the mixture was kept at room temperature for 10 minutes, then 42° C. for 1 hour.

Synthesis of a Second Strand

The reaction solution was combined with a reagent having the composition below, and the mixture was kept at 12° C. for 1 hour, then 22° C. for 1 hour and then 70° C. for 10 minutes.

Reaction Solution

| | |
|---|---|
| 5 × second strand synthesizing buffer | 11 μl |
| DEPC (diethyl pyrocarbonate)-treated dH$_2$O | 22.55 μl |
| E. coli DNA polymerase (3.5 U/μl) | 7.15 μl |
| E. coli RNase H/DNA ligase mixture | 1.1 μl. |

Then, this was combined with 2.2 μl of T4DNA polymerase (containing 2.2 U), and the mixture was kept for further 10 minutes.

(A-1-4) Preparation of a BodyMap Library

The cDNA library of the liver at onset stage and the cDNA library of the liver at recovery stage described above were treated with a second restriction endonuclease BglII and a third restriction endonuclease (MboI here, FIG. 2C-G) that produces the same end (FIG. 2C-H) as produced by cleavage with the second restriction endonuclease (FIG. 2C-G). Of the DNA fragments produced, an upstream fragment on the 5' end of cDNA was removed (FIG. 2C-G) and then the DNA strand carrying the vector was circularized (FIG. 2C-H). The resulting BodyMap library has a sequence ranging from the MboI site of cDNA to a site corresponding to mRNA polyA (FIG. 2C-H).

Cleavage with MboI

37° C., overnight (complete cleavage)

Reaction Solution

| cDNA library | |
|---|---|
| Universal buffer kit 10 × K for restriction endonuclease treatment (Takara, supplied with restriction endonuclease) | 10 μl |
| MboI (Takara, Ref. # 1069A, 10 U/μl) | 10 μl |
| dH$_2$O | 80 μl |

Cleavage with BglII
37° C., overnight (complete cleavage)

Reaction Solution

| cDNA cleaved with MboI | |
|---|---|
| Restriction endonuclease reaction buffer NEBuffer 3 (New England Biolabs. Ref. # 007-3) | 25 µl |
| BglII (New England Biolabs. Ref. # 144S (10 U/µl)) | 25 µl |
| dH₂O | 200 µl |

Circularization of DNA Cleaved with MboI/BglII

To 60 µl of DNA redissolved in dH₂O was added 60 µl of solution I in a ligation reaction kit (Takara, DNA Ligation Kit Ver. 2, Ref. # 6022), and this mixture was left at 16° C. overnight.

Isolation of Target DNA

Circularized DNA was used to transform *E. coli* competent cells JM109 (Takara, Ref. # 9052) (the colony incidence was approximately equal to that obtained by transformation with plasmid pBR922 used as a control), and target DNA was isolated from the transformants.

(A-2-1) Preparation of a Tag Sequence

The BodyMap library was cleaved with a first restriction endonuclease PmeI, then a type IIS restriction endonuclease BsgI (FIG. 2D-I, J), and the resulting DNA fragment containing a site corresponding to polyA was removed (FIG. 2D-J). The resulting linear plasmid was circularized to give a circular tag-containing plasmid (FIG. 2D-K). The tag sequence in the plasmid obtained here ranges from the first restriction endonuclease cleavage site (i.e., the third restriction endonuclease cleavage site) to the type IIS restriction endonuclease cleavage site in the direction of polyA end (FIG. 2D-J and K). Here, MboI was used as the third restriction endonuclease and BsgI was used as type IIS restriction endonuclease to give a tag sequence of 15–16 bases in length.

Cleavage of BodyMap Library with BsgI

| BodyMap library | |
|---|---|
| dH₂O (in which the library has been preliminarily dissolved) | 100 µl |
| Restriction endonuclease reaction buffer NEBuffer 4 (New England Biolabs. Ref. # 007-4) | 20 µl |
| BsgI (2 U/µl) | 5 µl |
| 0.8 mM S-adenosylmethionine solution (New England Biolabs. (32 mM, Ref. # 007-SAM) preliminarily diluted 40-fold in dH₂O) | 5 µl |
| dH₂O | 55 µl |

Reaction temperature and period: 37° C. for 8 hours.

Cleavage with PmeI

The BsgI cleavage reaction solution was combined with 2 µl of purified BSA solution (New England Biolabs, Reference #007-BSA (10 mg/ml)) and 4 µl of PmeI (New England Biolabs, Reference #560S), and the mixture was left at 37° C. overnight. The enzymatic reaction was stopped by heating the reaction solution at 65° C. for 20 minutes.

Circularization of the Linear Plasmid

To circularize the linear plasmid, the BsgI cleavage end must be blunted because the BsgI cleavage end projects by 2 bases toward the 5' side while the PmeI cleavage end is blunt (FIG. 2D-J). For blunting, DNA Blunting Kit (Takara, Ref. #6025) was used. The linear plasmid was heated after condition of 2 µl of 10× buffer and 16 µl of dH₂O at 70° C. for 5 minutes, and then left at 37° C. for 5 minutes with 2 µl of T4 DNA polymerase. The reaction solution was combined with 180 µl of TE buffer and DNA was extracted from the reaction solution with phenol/chloroform, then with chloroform, and the reaction solution was precipitated with ethanol in the presence of 1 µl of a glycogen solution as a precipitation aid (Boehringer Mannheim (currently Boehringer Ingelheim), 20 mg/ml solution, Ref. # 901393).

The resulting DNA was combined with 20 µl of dH₂O and 20 µl of solution I in a ligation reaction kit (Takara, DNA Ligation Kit Ver. 2, Ref. # 6022) for self-ligation at 16° C. overnight.

Isolation of Target DNA

The resulting circularized DNA was used to transform *E. coli* competent cells JM109 (Takara, Ref. #9052) (as compared with the same host transformed with the plasmid pBR322 used as a control), and the transformant colonies were isolated to give plasmid DNA. The number of plasmid DNA molecules estimated per µ 1 of the reaction solution was $1.3 \times 10^7$ molecules/µl for circularized DNA obtained from the cDNA library of the liver at onset stage and the cDNA library of the liver at recovery stage.

(A-2-2) Amplification of the Tag Sequence by PCR

The plasmid library containing a tag sequence described above was used as a template to amplify the tag sequence by PCR. The primers used were oligonucleotides having the sequences of the vector regions at both ends of the tag sequence of SEQ ID NO: 2 and SEQ ID NO: 3 (FIG. 2D-K)

```
ACGCCAGGGT TTTCCCAGTC ACGACG          (SEQ ID NO: 2)

(SEQ ID NO: 3)
ATGATTACGC CAAGCTTCCA TGCTGGCTCC GATCCGTTT
```

The resulting PCR amplification product is a DNA fragment of 110 bases in length having the tag sequence at the center and sequences derived from the vector at both ends (FIG. 2D-L).

PCR Reaction

| | |
|---|---|
| Tag sequence-containing plasmid library | 8 µl |
| 10 × PCR buffer (Amersham Pharmacia Biotech) | 160 µl |
| dNTP mix (2.5 mM each) (premix of equivalent amounts of 100 mM dNTP set from GIBCO BRL (Ref. #10297-018) in a 9-fold excess of dH₂O) | 128 µl |
| Primer solutions (10 µl) ("UP(-48) 26 mer" and "ZZ-makeMboI" having the sequences shown in FIG. 2D-K were used.) | 160 µl each |
| Taq polymerase (PERKIN ELMER, AmpliTaq Gold, Ref. # N808-0-240) | 8 µl |
| dH₂O | 976 µl. |

The above composition was used for PCR reaction under the conditions of 95° C. for 9 minutes→65 cycles of (95° C. for 15 seconds→72° C. for 90 seconds)→72° C. for 10 minutes→hold at 4° C. After completion of the reaction, proteinase K was added to the reaction solution at a final concentration of 500 µg/mg and the mixture was kept at 55° C.

(A-3-1) Preparation of a Concatemer

A DNA fragment containing the tag sequence described above convenient for ligation is excised from the PCR amplification product containing the tag sequence, and concatenated into a "concatemer". That is, PCR primers were designed in such a manner that the same recognition site as the third restriction endonuclease cleavage site is formed at both ends when the PCR amplification product is cleaved with the third restriction endonuclease. PCR primers here were designed to give a DNA fragment having the same terminal structure at 5'-cleavage site (the fourth restriction endonuclease cleavage site shown in FIG. 2C-E) and 3'-cleavage site (the fifth restriction endonuclease cleavage site shown in FIG. 2D-L) (upper line in FIG. 2E-M) because the PCR amplification product was cleaved with MboI.

If an adapter having the same form as that of the restriction endonuclease used to excise the above tag sequence at one end exists for ligating this tag sequence, a primer for PCR reaction from a sequence existing in this adapter can be designed (lower line in FIG. 2E-M). If ligation is performed using an adapter having a different form at the other end or using an adapter in smaller amounts as compared with the tag sequence, a concatemer containing many tag sequences can be formed. Here, an adapter obtained by annealing an oligo DNA having the nucleotide sequence of SEQ ID NO: 4 and an oligo DNA having the nucleotide sequence of SEQ ID NO: 5 (hereinafter referred to as "GATC-BglII") was used to have one end as described for excision with MboI (and BglII) and the other end blunted.

GATCGAGATCTGCAACCAGAGTCG (SEQ ID NO: 4)

CGACTCTGGTTGCAGATCTC. (SEQ ID NO: 5)

Excision of a DNA Fragment Containing a Tag Sequence

| Reaction solution PCR amplification product | |
|---|---|
| Universal Buffer Kit 10 × K for restriction endonuclease treatment (Takara, supplied with restriction endonuclease) | 90 μl |
| MboI (Takara, Ref. # 1069A, 10 U/μl) | 60 μl |
| dH$_2$O | 750 μl |

The above reaction solution was kept at 37° C. for 5 hours.

Then, the reaction product was dissolved in an appropriate amount of TE buffer, and electrophoresed on a 20% acrylamide gel, and the region corresponding to the size of the tag sequence region (about 20 bases) in ethidium bromide staining was cut out with a cutter. The cut-out region was triturated and the tag sequence region was extracted and recovered with TE buffer. To increase the recovery efficiency, recovery with TE buffer was repeated ten times after trituration. DNA was precipitated from the reaction solution with ethanol combined with a glycogen solution as a precipitation aid (Boehringer Mannheim (currently Boehringer Ingelheim), 20 mg/ml solution, Ref. #901393).

Insertion of a Ligation Adapter

| Tag sequence extraction solution | 5 μl |
|---|---|
| 0.23 M GATC-BglII adapter | 3 μl |
| 10 × T4 DNA ligase buffer | 1.5 μl |

| -continued | |
|---|---|
| (Takara, supplied with T4 DNA ligase below) | |
| 50 mM ATP | 1.5 μl |
| dH$_2$O | 3.1 μl |
| T4 DNA ligase (Takara, Ref. # 2011A) | 0.3 μl |
| T4 polynucleotide kinase | 0.6 μl. |

The above reaction solution was mixed and then kept at 37° C. for 2 hours.

(A-3-2) Amplification of the Concatemer

The resulting concatemer may be directly sequenced, but the concatemer was here amplified by PCR using PCR primers derived from the above tag ligation adapter. That is, an oligonucleotide having the nucleotide sequence of SEQ ID NO: 6 (hereinafter referred to as "makeNotI") was used as a PCR primer.

AACTTCGACTGCGGCCGCAGCTCTCGATC (SEQ ID NO: 6)

PCR Reaction

| Ligation reaction solution as above | 5 μl |
|---|---|
| 10 × PCR buffer | 100 μl |
| (Amersham Pharmacia Biotech) | |
| dNTP mix (2.5 mM each) | 80 μl |
| makeNotI primer (20 μM) | 200 μl |
| dH$_2$O | 610 μl |
| Taq polymerase | 5 μl |
| (PERKIN ELMER, AmpliTaq Gold, Ref. # N808-0240). | |

The above composition was used for PCR reaction under the conditions of 95° C. for 9 minutes→10 cycles of (95° C. for 20 seconds→40° C. for 3 minutes→[temperature rise for 1.5 minutes]→72° C. for 1 minutes)→60 cycles of (95° C. for 20 seconds→72° C. for 2 minutes)→72° C. for 15 seconds→hold at 4° C. After completion of the reaction, proteinase K was added at a final concentration of 500 μg/ml for enzyme treatment at 55° C.

(A-3-3) Cloning of the Concatemer

The concatemer amplified by PCR was cloned before sequencing.

The cloning vector used for sequencing was pKF3 (Enforcement Cloning Vector pKF3, Ref. # 3100 available from Takara), and NotI site was used as an insertion site.

Cleavage of the Concatemer PCR Amplification Product with NotI

| Reaction solution Concatemer PCR amplification product | |
|---|---|
| Universal Buffer Kit 10 × H for restriction endonuclease treatment (Takara, supplied with restriction endonuclease) | 100 μl |
| 0.1% BSA solution | 100 μl |
| (Takara, supplied with restriction endonuclease) | |
| 0.1% Triton X-100 | 100 μl |
| (Takara, supplied with restriction endonuclease) | |
| NotI (Takara, Ref. # 1166A, 10 U/μl) | 50 μl |
| dH$_2$O | 650 μl. |

The above reaction solution was kept at 37° C. overnight, and DNA was extracted from the reaction solution with phenol/chloroform, then chloroform and precipitated with ethanol.

Cleavage of pKF3 DNA with NotI

| | |
|---|---|
| pKF3 DNA (Takara, 500 μg/ml) | 2 μl |
| Universal Buffer Kit 10 × H for restriction endonuclease treatment (Takara, supplied with restriction endonuclease) | 2 μl |
| 0.1% BSA solution (Takara, supplied with restriction endonuclease) | 2 μl |
| 0.1% Triton X-100 (Takara, supplied with restriction endonuclease) | 2 μl |
| NotI (Takara, Ref. # 1166A, 10 U/μl) | 1 μl |
| dH$_2$O | 11 μl. |

Ligation of the Concatemer PCR Amplification Product with the Cloning Vector

| Ligation reaction solution PCR amplification product/NotI digest | |
|---|---|
| pKF3/NotI digest | 4 μl |
| Ligation Reaction kit, solution I (Takara, included in DNA Ligation Kit Ver. 2, Ref. # 6022). | 4 μl |

The ligation reaction solution was kept at 16° C. overnight to prepare a circular plasmid in which the concatemer has been integrated.

Transformation

The host used was *E. coli* TH2 competent cells (available from Takara as "Enforcement Cloning System pKF3", Ref. # 6086 in combination with pKF3). When a streptomycin-containing medium was used, non-transformants could not grow while only strains transformed with foreign genes could grow because the streptomycin-sensitive ribosome protein rpsL gene is inserted into the pKF3 vector.

The circular plasmid integrated with the concatemer was added to 100 μl of *E. coli* TH2 on ice and gently blended and allowed to stand for 30 minutes. Then, the mixture was incubated at 42° C. for 45 seconds and allowed to stand on ice for 2 minutes, and SOC medium preliminarily kept at a temperature of 37° C. was added to a volume of 1 ml. The mixture was shaken at 37° C. for 1 hour. Then, an appropriate amount of the mixture was plated on an LB agar plate containing 12 μg/ml of chloramphenicol and 50 μg/ml of streptomycin and incubated overnight at 37° C., and the colonies produced were isolated.

(A-3-4) Sequencing of the Concatemer

Thus cloned concatemer was sequenced.

The cloned concatemer was first amplified by PCR using the sequence of the cloning vector as a primer.

PCR Amplification

| Plasmid DNA from isolated colonies (PCR template) | |
|---|---|
| 10 × PCR buffer (Amersham Pharmacia Biotech) | 1.0 μl/tube |
| dNTP mix (10 mM each) | 0.2 μl/tube |
| 20 μM pKF3 primer F3 (Takara, Ref. # 3892) | 0.25 μl/tube |
| 20 μM pKF3 primer R2 (Takara, Ref. # 3894) | 0.25 μl/tube |
| Taq polymerase (Amersham Pharmacia Biotech) | 0.05 μl/tube |
| dH$_2$O | 8.25 μl/tube |

Reaction conditions: 94° C. for 1 minute→45 cycles of (94° C. for 20 seconds→50° C. for 1 minute→72° C. for 5 minutes→hold at 4° C.].

Sequencing

To 2 μl of a 5-fold dilution of the above PCR reaction solution in dH$_2$O were added 0.3 μl each of Exonuclease I and Alkaline Phosphatase from shrimp (available from USB as PCR product pre-sequencing kit, Ref. # US70995) and 2.4 μl of dH$_2$O, and the mixture was kept at 37° C. for 1 hour. To 5 μl of the reaction solution were added 1 μl of pKF3-R2 (1.6 pM) as a sequencing primer and 4 μl of a mixed sequencing solution (Big Dye from PE Applied Biosystems) to perform a sequencing reaction under reaction conditions as follows: 96° C. for 2 minutes→25 cycles of (96° C. for 15 seconds→50° C. for 5 seconds→60° C. for 4 minutes)→hold at 4° C.

After completion of the reaction, unreacted materials were removed from the reaction solution, and dried by heat. The resulting DNA was dissolved in 7.5 μl of dH$_2$O and the DNA solution was heated at 95° C. for 4 minutes and then transferred to a capillary sequencer 3700 (PE applied Biosystems).

(A-4-1) Classification and Counting of Tags

Among the sequences obtained by sequencer analysis, the sequence flanked by the third restriction endonuclease recognition site ("GATC" in FIG. 2E-M) and the sequence derived from the primers for PCR ("AAACG" in FIG. 2E-M) was read out from the nucleotide sequence of the concatemer because it corresponds to a tag sequence. During then, the orientation of the sequence from the primers was checked to see if it was forward (the tag sequence followed by "AAACG" in FIG. 2E-M) or reverse (the tag sequence preceded by "CGTTT" (FIG. 2E-M)), and if it was reverse, the sequence was read out as if it were forward. The molecular types of the resulting tag sequences were classified on the basis of the sequences and the number of tag sequences belonging to each class was counted. That is, the sequences flanked by "GATC" and "AAACGGATC" in the nucleotide sequences of the resulting concatemer were picked up and recorded. The sequences flanked by "GATC-CGTTT" and "GATC" were recorded as complementary strands thereto.

The procedure described above gave a total of 4085 types of tag sequences consisting of 3609 sequences from onset stage livers (a total of 31177 members) and 1229 sequences from recovery stage livers (a total of 12220 members).

(A-4-2) Analysis of the Counting Results of Tag Sequences

Of the 4085 tag sequences, those showing a significant difference in expression frequency between onset stage and recovery stage livers were picked up. The results showed that the tags having the nucleotide sequence of SEQ ID NO: 7 accounted for 0.24% of the total of tags from recovery stage livers as compared with only 0.003% of the total of tags from onset stage livers. This means that mRNA having the nucleotide sequence of SEQ ID NO: 7, therefore the polypeptide encoded by the mRNA showed a production level specifically lowered in diseased livers.

GATCTCGCACTGCAG (SEQ ID NO: 7).

[B] Identification of Polypeptide Having Specifically Suppressed Production in the Liver of Hepatitis Patients

(B-1) Identification of a Gene Having the Nucleotide Sequence of a Tag and Acquisition of the Gene A gene having the nucleotide sequence of SEQ ID NO: 7 was searched through data bases to give a human expression gene tagged EST having the nucleotide sequence completely identical with SEQ ID NO: 7 (GenBank accession number AI828136) (SEQ ID NO: 13).

On the basis of the sequence of thus obtained tagged EST, PCR primers having the nucleotide sequences of SEQ ID NO: 8 and SEQ ID NO: 9 were designed, respectively.

AGACCTGCGGCAAGTCCTTC (SEQ ID NO: 8)
CAGCTTCTCGAAGCGCTTCC (SEQ ID NO: 9).

The cDNA library used to isolate the target gene was a human cDNA library series human liver available from Takara (plasmid type, Ref. # 9505).

The cDNA library plasmid was subjected to a PCR reaction using the PCR primer pair shown above. The PCR reaction product was isolated by electrophoresis on 4% agarose gel.

Preparation of a cDNA Library

To 2 µl of the cDNA library was added 50 µl of an E. coli suspension for transformation (ElectroMax DH12S Cell, GIBCO-BRL) to perform transformation by electroporation according to a standard method. Then, the suspension was shaken with 1 ml of SOC at 37° C. for 55 minutes, and thoroughly mixed with 6.5 ml of SOC and 2.5 ml of filter-sterilized 80% glycerol solution by 0.45 µm filter. This suspension contained about 50000 transformants per µ 1. This suspension was mixed with 300 ml of 2×YT medium per 20 µl of the suspension to a density of several thousands of transformants per well, and a 1 ml aliquot was dispensed in each well of a 96-deep well plate and cultured with shaking at 37° C. overnight. Then, plasmids were extracted from each well as conventionally.

| PCR reaction | |
|---|---|
| 10 × PCR buffer (Amersham Pharmacia Biotech) | 1.0 µl/tube |
| 10 mM dNTP mix | 0.2 µl/tube |
| 10 µM PCR primer solution | 1.0 µl/tube |
| Taq polymerase (Amersham Pharmacia Biotech) | 0.05 µl/tube |
| template DNA (2 ng/µl, plasmid prepared as above) | 1.0 µl/tube |
| dH$_2$O | 6.75 µl/tube |

Reaction conditions: reaction at 94° C. for 1 minute→45 cycles of (94° C. for 20 seconds→50° C. for 1 minute→72° C. for 30 seconds)→72° C. for 5 minutes→hold at 4° C.

Plasmid samples containing the target gene obtained here still contained much other genes than the target, so that the amount of transformants per well was adjusted to several hundreds per well and the same operation as described above was performed to select and identify wells containing clones carrying the target gene again.

One µ 1 of the plasmids obtained were transformed as described above, and the transformants were appropriately diluted in such a manner that the transformants form colonies consisting of single clones, and such a dilution was plated on an LB agar plate containing 100 µg/ml ampicillin and incubated at 37° C. overnight. Each colony obtained was subjected to PCR reaction using the PCR primers shown above, and clones carrying plasmids showing amplification products (clone #76) were selected as those containing the target gene.

(B-2) Sequencing of the Gene and Determination of the Amino Acid Sequence of the Polypeptide Encoded Thereby Clone #76 was inoculated in 100 ml of 2×YT liquid medium and cultured with shaking at 37° C. overnight, and the cultured cells were used to prepare a plasmid carrying clone # 76 according to a standard method. This plasmid DNA was dissolved at about 0.5 µg/µ 1 and sequenced by using a PCR primer pair of the sequences shown in SEQ ID NO: 8 and SEQ ID NO: 9 and promoter sequences of T7 and T3 RNA polymerases in this library as sequencing primers.

| Sequencing | |
|---|---|
| template DNA (0.5 µg/µl) | 1 µl |
| 1.6 pM sequencing primer solution | 2 µl |
| BigDye (PE Applied Biosystems) | 8 µl |
| dH$_2$O | 9 µl |

Reaction conditions: reaction at 96° C. for 1 minute→25 cycles of (96° C. for 15 seconds→50° C. for 5 second→60° C. for 4 minutes)→hold at 4° C.

Figure 3:
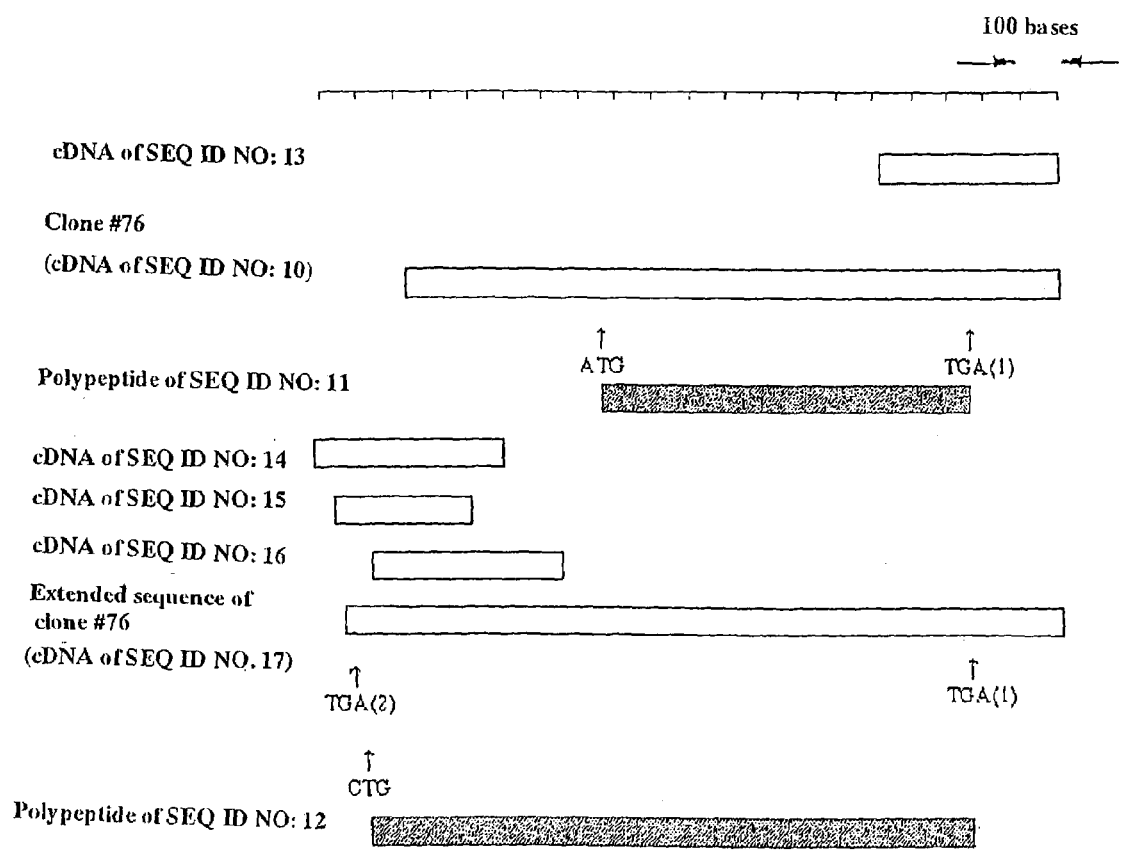
FIG. 3 is a schematic view showing cDNAs encoding polypeptides of the present invention.

Unreacted dye was removed from the PCR reaction product by gel permeation with Sephadex G-50, and recovered portions were dried at 80° C. and combined with 7.5 µl of water and then heated at 90° C. for 2 minutes. Then, this PCR reaction product was subjected to DNA sequence analysis on a DNA sequencer (ABI 3700 capillary sequencer, PE Applied Biosystems) to give a sequence of about 500 bp in each case. The length of the insert existing in the plasmid was separately preexamined by agarose gel electrophoresis for this sequence of about 500 bp to show that it was shorter than the insert, suggesting the existence of an unsequenced region. Thus, a primer for sequence analysis was separately redesigned from the end of the above sequence of about 500 bp and sequencing reaction was repeated to determine the gene sequence of a total of 1770 bases (SEQ ID NO: 10) (FIG. 3).

The amino acid sequence encoded by this nucleotide sequence of SEQ ID NO: 10 was determined using a computer software ORFinder that converts gene sequences into amino acids codes, which is publicly available through the web-site for the National Center for Biotechnology Information, National Library of Medicine, National Institutes of Health (Bethesda, Md.) hereby incorporated by reference as if fully set forth herein. A translation stop codon "TGA(1)" and a translation start codon "ATG" were found in this nucleotide sequence to show the presence of a region encoding a polypeptide having the amino acid sequence of SEQ ID NO: 11.

It was found that a structural feature of a zinc finger motif having 2 Cys molecules and 2 His molecules recurs five times in about 12 amino acid residues at the C-terminus in this amino acid sequence. This motif is a structure characteristic of a transcription factor involved in the transcription of DNA via zinc atom bound to this region.

To further analyze the upstream of cDNA of SEQ ID NO: 10 (5' side), upstream sequences were searched through BLAST to reveal identity in ESTs of GenBank accession Nos. AI091320 (SEQ ID NO: 14), hereby incorporated by reference as if fully set forth herein, AI089062 (SEQ ID NO: 15), hereby incorporated by reference as if fully set forth herein, and AW089826 (SEQ ID NO: 16), hereby incorporated by reference as if fully set forth herein. The nucleotide sequences of SEQ ID NO: 14, SEQ IE NO: 15 and SEQ ID NO: 16 were assembled with the sequence of clone #76 to give an extended sequence of clone #76 (SEQ ID NO: 17). Analysis of the extended sequence of clone #76 showed the presence of a translation stop codon "TGA(2)" spanning nucleotides 102–104 of the nucleotide sequence of SEQ ID NO: 17 in addition to and upstream of the "TGA(1)" shown above. This indicated that the amino acid sequence of the polypeptide encoded by this gene begins downstream of "TGA(2)". Thus, the nearest translation start codon to this stop codon was searched, but any "ATG" codon was not found before the "ATG" codon above. However, a "CTG" codon was found spanning nucleotides 114–116 of the nucleotide sequence of SEQ ID NO: 17 downstream of "TGA(2)". In connection with this "CTG" codon, Takayama S. et al. (Takayama S., et al.: Cancer Res. 58 (14) 3116 (1998), hereby incorporated by reference as if fully set forth herein) describes that BAG-1 gene belonging to Bcl-2 family encodes a protein called BAG-IL translated from "CTG" upstream of "ATG" in addition to the molecule translated from "ATG" and that this BAG-IL is seldom produced in normal tissue cells but a long chain, BAG-1L is produced in tumor cell lines via translation started from "CTG" codon. Thus, the gene of SEQ ID NO: 17 also seems to be translated from this "CTG" codon. The polypeptide produced via translation from the "CTG" codon has the amino acid sequence of SEQ ID NO: 12.

Verification of Intracellular Localization

An expression vector that expresses a fused peptide having HA-Tag (hemagglutinin) attached to the N-terminus of SEQ ID NO: 11 was designed and constructed as follows.

First, the cDNA encoding the polypeptide of SEQ ID NO: 11 was amplified by PCR. During then, HA-tag sequence was integrated into the primer sequence corresponding to the 5' end, i.e., the N-terminus of the polypeptide (HA-#76-5'-end primer) (sequence: ctctggtaccatgtatccttatgatgt-gcctgattatgcttctctgatgccaggcatggtgcccgg (SEQ ID NO: 18) containing a region encoding HA-tag, KpnI site as a restriction endonuclease recognition site for cloning and the N-terminal eDNA sequence of SEQ ID NO: 11). After amplification by PCR, the amplification product was integrated into a plasmid expression vector, and the constructed plasmid expression vector DNA was prepared in large quantities. This expression vector was transfected into HepG2 cells or Chang liver cells.

Transfection was performed with FuGENE6 Transfection Reagent from Roche (Code 1815075) according to the protocol of the manufacturer. After 48 hours, cells were fixed and treated with rabbit IgG-anti-HA-Tag antibody as a primary antibody and stained with FITC labeled anti-rabbit IgG antibody as a secondary antibody, and observed under a fluorescent microscope.

As a result, fluorescent staining was observed in cell nuclei of both HepG2 and Chang liver cells. Staining of nuclei was not homogeneous, but especially strong at the nuclear body-like structure in nuclei.

Change of the Expression Level in Diseased Livers

The expression level of #76 gene in specimens obtained by biopsy from the liver of 6 hepatitis patients was examined. A non-cancerous portion of the liver extracted by hepatic cancer surgery was used as non-hepatitis control. The expression level was determined with a TaqMan kit from PE Biosystems. Primer sequences were 76 Mbolcut-3-440F: atgttccactgcccatacgag (SEQ ID NO: 19) and 76 MboI-3-532R: ctttcctttccgatgcacaag (SEQ ID NO: 20). The sequence of TaqMan probe was 76 Mbolcut-3-485T: ctcag-cagcttccagaaccacgtcaa (SEQ ID NO: 21). Experimental procedures were performed following the protocol of the manufacturer.

As a result, the expression level of #76 gene in the control was 0.415 in contrast to the expression level in the liver of hepatitis patients of 0.107-0.167, which was much lower than the control by 25%-40%.

This result shows that #76 gene is generally less expressed in hepatitis patients. Therefore, it can be concluded that the polypeptides of SEQ ID NOS: 11 and 12 encoded by #76 gene are universally decreased in hepatitis patients.

The foregoing results showed that the polypeptide showing a production level specifically lowered in diseased livers is both or either one of a polypeptide having the amino acid sequence of SEQ ID NO: 11 and a polypeptide having the amino acid sequence of SEQ ID NO: 12.

Thus, the polypeptide having the amino acid sequence shown in SEQ ID NO: 11 or SEQ ID NO: 12 was found to have a production level specifically lowered in diseased livers.

INDUSTRIAL APPLICABILITY

A novel diagnostic means can be provided by finding a polypeptide showing a production level specifically lowered in the liver having inflammation.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. 2000-191379, filed on Jun. 26, 2000, hereby incorporated by reference as if fully set forth herein.

The invention claimed is:

1. An isolated or synthesized polypeptide having the amino acid sequence of SEQ ID NO: 11.

2. A diagnostic kit for diagnosing hepatitis by determining the production level of the polypeptide of claim 1 in the liver, said kit comprising a container which contains said polypeptide.

3. The diagnostic kit of claim 1, wherein said kit further comprises an antibody specific for said polypeptide of claim 1 or a part thereof.

4. The diagnostic kit of claim 3, wherein said antibody is a polyclonal antibody.

5. The diagnostic kit of claim 3, wherein said antibody is a monoclonal antibody.

6. The diagnostic kit of claim 3, wherein said antibody is labeled with an enzyme involved in a color development reaction.

7. The diagnostic kit of claim 3, wherein said antibody is labeled with a radioisotope.

8. The diagnostic kit of claim 3, wherein said antibody is labeled with a stained colloid.

9. The diagnostic kit of claim 8, wherein said stained colloid is a gold colloid or a selenium colloid.

10. The diagnostic kit of claim 3, wherein said antibody is labeled with a fluorescent compound.

11. The diagnostic kit of claim 3, wherein said antibody is labeled with a chemiluminescent compound.

* * * * *

SEQUENCE LISTING

<160> NUMBER OF SEQ ID NOS: 18

<210> SEQ ID NO 1
<211> LENGTH: 48
<212> TYPE: DNA
<213> ORGANISM: Artificial Sequence
<220> FEATURE:
<223> OTHER INFORMATION: Synthetic DNA

<400> SEQUENCE: 1
gaattcgtgc agatctcaca ctgcagagat ccaacagcat ggaagctt                48

<210> SEQ ID NO 2
<211> LENGTH: 26
<212> TYPE: DNA
<213> ORGANISM: Artificial Sequence

```
<220> FEATURE:
<223> OTHER INFORMATION: Synthetic DNA

<400> SEQUENCE: 2
acgccagggt tttcccagtc acgacg                                          26

<210> SEQ ID NO 3
<211> LENGTH: 39
<212> TYPE: DNA
<213> ORGANISM: Artificial Sequence
<220> FEATURE:
<223> OTHER INFORMATION: Synthetic DNA

<400> SEQUENCE: 3
atgattacgc caagcttcca tgctggctcc gatccgttt                            39

<210> SEQ ID NO 4
<211> LENGTH: 24
<212> TYPE: DNA
<213> ORGANISM: Artificial Sequence
<220> FEATURE:
<223> OTHER INFORMATION: Synthetic DNA

<400> SEQUENCE: 4
gatcgagatc tgcaaccaga gtcg                                            24

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
cgactctggt tgcagatctc                                                 20

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
aacttcgact gcggccgcag ctctcgatc                                       29

<210> SEQ ID NO 7
<211> LENGTH: 15
<212> TYPE: DNA
<213> ORGANISM: Artificial Sequence
<220> FEATURE:
<223> OTHER INFORMATION: Synthetic DNA

<400> SEQUENCE: 7
gatctcgcac tgcag                                                      15

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
agacctgcgg caagtccttc                                                 20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
cagcttctcg aagcgcttcc                                          20

<210> SEQ ID NO 10
<211> LENGTH: 1770
<212> TYPE: DNA
<213> ORGANISM: Homo sapiens

<400> SEQUENCE: 10

```
ggaagaaaag gcggcgacgc aacgtgaact gcctgaagaa cgtggtgatc tggtacgagg        60
accacaagca ccgctgcccg tacgagccgc acctggcgga gctagacccc acttttggcc       120
tgtacaccac ggccgtgtgg cagtgcgaag ctggccaccg ctacttccag gacctgcatt       180
cgccctgaa gccctcagc gactcagacc ctgacagtga caaagtgggc aatgggctgg          240
tggctggcag ctctgactca tccagctctg gctctgcctc tgactctgag gagtctcctg       300
agggccagcc ggtcaaggct gcggcagcgg cagcggcagc gacgcccacc agcccggtgg       360
gcagcagcgg gctcatcact caggagggcg tgcacattcc ctttgacgtc caccacgtgg       420
aaagcctggc cgagcagggt accccgctgt gctccaaccc agcaggcaat gggcctgaag       480
ccctggagac agtggtgtgc gtgccggtgc ctgtgcaagt gggtgcgggc cccagcgccc       540
tctttgagaa cgtgccccag gaggccctgg gtgaggtggt ggccagctgc cccatgccag       600
gcatggtgcc cggctcacag gtgatcatca ttgcgggccc tggttacgac gctctcacgg       660
ccgagggcat tcacctcaac atggcagcag gcagcggtgt ccccggcagt ggactgggcg       720
aggaggtgcc ctgtgccatg atggagggtg tggcagccta cacccagaca gagcccgagg       780
gtagccagcc tagcaccatg gacgccaccg cagtagcagg catcgagacc aagaaagaga       840
aggaggacct gtgcttgcta aagaaggagg agaaggagga gccagtagcc ccggagctgg       900
caacaacggt gcctgagagc gcagagcctg aggcagaggc ggacggggag gagctggacg       960
gcagcgacat gtcagccatc atctatgaaa tccccaagga gcctgagaag aggcggcgga      1020
gcaagcggtc gcgggtgatg gatgctgacg gcctgctcga gatgttccac tgcccatacg      1080
agggctgcag ccaagtctac gtggccctca gcagcttcca gaaccacgtc aatcttgtgc      1140
atcggaaagg aaagaccaaa gtgtgccctc atcctggctg tggcaagaag ttctatttat      1200
ccaaccacct gcggcggcac atgatcatcc attcaggtgt ccgtgaattc acctgcgaga      1260
cctgcggcaa gtccttcaag aggaagaacc acctggaggt acatcggcgc acccacaccg      1320
gcgagacccc cctgcagtgc gagatctgtg ctaccagtg ccggcagcgc gcgtcgctca       1380
actggcacat gaagaagcac actgcggagg tgcagtacaa cttcacgtgc gatcgctgcg      1440
ggaagcgctt cgagaagctg gacagcgtca agttccacac gctcaaaagc cacccggatc      1500
acaagcccac ctgacccacc tgaccactga ccgcccctat ttattcgtcc gctcggacac      1560
cacgcccggg cttgccgggg cctggacagc tgcgagggcc gccgaccg cgggccggaa        1620
ggaggcgccc ccgcccgcc ccagagctgg gccccctggg caggttcccc accccgcccc       1680
accgcatcct tctcggagct ggtgcctggg gctgcattgc tggaactgtg tcaagagagc      1740
agagtgagat taaagagcga gaaaggaaaa                                      1770
```

```
<210> SEQ ID NO 11
<211> LENGTH: 306
<212> TYPE: PRT
<213> ORGANISM: Homo sapiens
<220> FEATURE:
<221> NAME/KEY: ZN_FING
<222> LOCATION: (160)..(183)
<223> OTHER INFORMATION:
<220> FEATURE:
<221> NAME/KEY: ZN_FING
<222> LOCATION: (191)..(213)
<223> OTHER INFORMATION:
<220> FEATURE:
<221> NAME/KEY: ZN_FING
<222> LOCATION: (221)..(241)
<223> OTHER INFORMATION:
<220> FEATURE:
<221> NAME/KEY: ZN_FING
<222> LOCATION: (249)..(269)
<223> OTHER INFORMATION:
<220> FEATURE:
<221> NAME/KEY: ZN_FING
<222> LOCATION: (279)..(300)
<223> OTHER INFORMATION:

<400> SEQUENCE: 11
```

Met Pro Gly Met Val Pro Gly Ser Gln Val Ile Ile Ala Gly Pro
1               5                   10                  15

Gly Tyr Asp Ala Leu Thr Ala Glu Gly Ile His Leu Asn Met Ala Ala
            20                  25                  30

Gly Ser Gly Val Pro Gly Ser Gly Leu Gly Glu Glu Val Pro Cys Ala
        35                  40                  45

Met Met Glu Gly Val Ala Ala Tyr Thr Gln Thr Glu Pro Glu Gly Ser
    50                  55                  60

Gln Pro Ser Thr Met Asp Ala Thr Ala Val Ala Gly Ile Glu Thr Lys
65                  70                  75                  80

Lys Glu Lys Glu Asp Leu Cys Leu Leu Lys Glu Glu Lys Glu Glu
                85                  90                  95

Pro Val Ala Pro Glu Leu Ala Thr Thr Val Pro Glu Ser Ala Glu Pro
            100                 105                 110

Glu Ala Glu Ala Asp Gly Glu Glu Leu Asp Gly Ser Asp Met Ser Ala
        115                 120                 125

Ile Ile Tyr Glu Ile Pro Lys Glu Pro Glu Lys Arg Arg Arg Ser Lys
    130                 135                 140

Arg Ser Arg Val Met Asp Ala Asp Gly Leu Leu Glu Met Phe His Cys
145                 150                 155                 160

Pro Tyr Glu Gly Cys Ser Gln Val Tyr Val Ala Leu Ser Ser Phe Gln
                165                 170                 175

Asn His Val Asn Leu Val His Arg Lys Gly Lys Thr Lys Val Cys Pro
            180                 185                 190

His Pro Gly Cys Gly Lys Lys Phe Tyr Leu Ser Asn His Leu Arg Arg
        195                 200                 205

His Met Ile Ile His Ser Gly Val Arg Glu Phe Thr Cys Glu Thr Cys
    210                 215                 220

Gly Lys Ser Phe Lys Arg Lys Asn His Leu Glu Val His Arg Arg Thr
225                 230                 235                 240

His Thr Gly Glu Thr Pro Leu Gln Cys Glu Ile Cys Gly Tyr Gln Cys
                245                 250                 255

Arg Gln Arg Ala Ser Leu Asn Trp His Met Lys Lys His Thr Ala Glu
            260                 265                 270

-continued

```
Val Gln Tyr Asn Phe Thr Cys Asp Arg Cys Gly Lys Arg Phe Glu Lys
            275                 280                 285

Leu Asp Ser Val Lys Phe His Thr Leu Lys Ser His Pro Asp His Lys
        290                 295                 300

Pro Thr
305

<210> SEQ ID NO 12
<211> LENGTH: 528
<212> TYPE: PRT
<213> ORGANISM: Homo sapiens
<220> FEATURE:
<221> NAME/KEY: ZN_FING
<222> LOCATION: (382)..(405)
<223> OTHER INFORMATION:
<220> FEATURE:
<221> NAME/KEY: ZN_FING
<222> LOCATION: (413)..(435)
<223> OTHER INFORMATION:
<220> FEATURE:
<221> NAME/KEY: ZN_FING
<222> LOCATION: (443)..(463)
<223> OTHER INFORMATION:
<220> FEATURE:
<221> NAME/KEY: ZN_FING
<222> LOCATION: (471)..(491)
<223> OTHER INFORMATION:
<220> FEATURE:
<221> NAME/KEY: ZN_FING
<222> LOCATION: (501)..(522)
<223> OTHER INFORMATION:

<400> SEQUENCE: 12

Leu Ser Pro Leu Gln Cys Asp Thr Pro Ser Leu Gln Arg Lys Pro Trp
1               5                   10                  15

Glu Gln Val Pro Lys Lys Pro Lys Arg Lys Arg Arg Arg Arg Arg Asn
            20                  25                  30

Val Asn Cys Leu Lys Asn Val Val Ile Trp Tyr Glu Asp His Lys His
        35                  40                  45

Arg Cys Pro Tyr Glu Pro His Leu Ala Glu Leu Asp Pro Thr Phe Gly
    50                  55                  60

Leu Tyr Thr Thr Ala Val Trp Gln Cys Glu Ala Gly His Arg Tyr Phe
65                  70                  75                  80

Gln Asp Leu His Ser Pro Leu Lys Pro Leu Ser Asp Ser Asp Pro Asp
                85                  90                  95

Ser Asp Lys Val Gly Asn Gly Leu Val Ala Gly Ser Ser Asp Ser Ser
            100                 105                 110

Ser Ser Gly Ser Ala Ser Asp Ser Glu Glu Ser Pro Glu Gly Gln Pro
        115                 120                 125

Val Lys Ala Ala Ala Ala Ala Ala Thr Pro Thr Ser Pro Val
    130                 135                 140

Gly Ser Ser Gly Leu Ile Thr Gln Glu Gly Val His Ile Pro Phe Asp
145                 150                 155                 160

Val His His Val Glu Ser Leu Ala Glu Gln Gly Thr Pro Leu Cys Ser
                165                 170                 175

Asn Pro Ala Gly Asn Gly Pro Glu Ala Leu Glu Thr Val Val Cys Val
            180                 185                 190

Pro Val Pro Val Gln Val Gly Ala Gly Pro Ser Ala Leu Phe Glu Asn
        195                 200                 205

Val Pro Gln Glu Ala Leu Gly Glu Val Val Ala Ser Cys Pro Met Pro
    210                 215                 220
```

-continued

```
Gly Met Val Pro Gly Ser Gln Val Ile Ile Ala Gly Pro Gly Tyr
225                 230                 235                 240

Asp Ala Leu Thr Ala Glu Gly Ile His Leu Asn Met Ala Ala Gly Ser
            245                 250                 255

Gly Val Pro Gly Ser Gly Leu Gly Glu Val Pro Cys Ala Met Met
        260                 265                 270

Glu Gly Val Ala Ala Tyr Thr Gln Thr Glu Pro Glu Gly Ser Gln Pro
    275                 280                 285

Ser Thr Met Asp Ala Thr Ala Val Ala Gly Ile Glu Thr Lys Lys Glu
    290                 295                 300

Lys Glu Asp Leu Cys Leu Leu Lys Lys Glu Lys Glu Glu Pro Val
305                 310                 315                 320

Ala Pro Glu Leu Ala Thr Thr Val Pro Glu Ser Ala Glu Pro Glu Ala
            325                 330                 335

Glu Ala Asp Gly Glu Glu Leu Asp Gly Ser Asp Met Ser Ala Ile Ile
            340                 345                 350

Tyr Glu Ile Pro Lys Glu Pro Glu Lys Arg Arg Arg Ser Lys Arg Ser
        355                 360                 365

Arg Val Met Asp Ala Asp Gly Leu Leu Glu Met Phe His Cys Pro Tyr
370                 375                 380

Glu Gly Cys Ser Gln Val Tyr Val Ala Leu Ser Ser Phe Gln Asn His
385                 390                 395                 400

Val Asn Leu Val His Arg Lys Gly Lys Thr Lys Val Cys Pro His Pro
                405                 410                 415

Gly Cys Gly Lys Lys Phe Tyr Leu Ser Asn His Leu Arg Arg His Met
            420                 425                 430

Ile Ile His Ser Gly Val Arg Glu Phe Thr Cys Glu Thr Cys Gly Lys
        435                 440                 445

Ser Phe Lys Arg Lys Asn His Leu Glu Val His Arg Arg Thr His Thr
450                 455                 460

Gly Glu Thr Pro Leu Gln Cys Glu Ile Cys Gly Tyr Gln Cys Arg Gln
465                 470                 475                 480

Arg Ala Ser Leu Asn Trp His Met Lys Lys His Thr Ala Glu Val Gln
            485                 490                 495

Tyr Asn Phe Thr Cys Asp Arg Cys Gly Lys Arg Phe Glu Lys Leu Asp
        500                 505                 510

Ser Val Lys Phe His Thr Leu Lys Ser His Pro Asp His Lys Pro Thr
    515                 520                 525
```

<210> SEQ ID NO 13
<211> LENGTH: 624
<212> TYPE: DNA
<213> ORGANISM: Homo sapiens

<400> SEQUENCE: 13

```
ttttttcttt ttttgctctt taatctcact ctgctctctt gacacagttc cagcaatgca    60
gccccaggca ccagctccga gaaggatgcg gtggggcggg gtggggaacc tgcccagggg   120
gcccagctct ggggcggggc ggggggcgcct ccttccggcc cgcggtccgg gcggccctcg   180
cagctgtcca ggccccggca agcccgggcg tggtgtccga gcggacgaat aaataggggc   240
ggtcagtggt caggtgggtc aggtgggctt gtgatccggg tggcttttga gcgtgtggaa   300
cttgacgctg tccagcttct cgaagcgctt cccgcagcga tcgcacgtga agttgtactg   360
cacctccgca gtgtgcttct tcatgtgcca gttgagcgac gcgcgctgcc ggcactggta   420
```

| gccacagatc tcgcactgca gggggtctc gccggtgtgg gtgcgccgat gtacctccag | 480 |
| gtggttcttc ctcttgaagg acttgccgca gtctcgcag gtgaattcac ggacacctga | 540 |
| atggatgatc atgtgccgcc gcaggtggtt ggataaatag aacttcttgc cacagccagg | 600 |
| atgagggcac acttttggtc tttc | 624 |

<210> SEQ ID NO 14
<211> LENGTH: 501
<212> TYPE: DNA
<213> ORGANISM: Homo sapiens
<220> FEATURE:
<221> NAME/KEY: misc_feature
<222> LOCATION: (476)..(476)
<223> OTHER INFORMATION: n = a, c, g, or t

<400> SEQUENCE: 14

| gcggccgcca cggacggaga ctgaggctca gagggacaa gacctgcttg aggtcacaca | 60 |
| ggcagttgag agcagagctg agtcttgaac ttgggtctgg ctgatacccca agactgtccc | 120 |
| cactgcaatg tgacactccc agcctccagc ggaagccttg ggagcaggtc cccaaaaagc | 180 |
| caaagcggaa gaaaaggcgg cgacgcaacg tgaactgcct gaagaacgtg gtgatctggt | 240 |
| acgaggacca caagcaccgc tgcccgtacg agccgcacct ggcggagcta gaccccactt | 300 |
| ttggcctgta caccacggcc gtgtggcagt gcgaagctgg ccaccgctac ttccaggacc | 360 |
| tgcattcgcc cctgaagccc ctcagcgact cagaccctga cagtgacaaa ggtaggtctg | 420 |
| cagggcgagg gcataggg ggccgcccat ttctggggc ttcttacgag ccctangcta | 480 |
| gcatcacaaa cagaatagca g | 501 |

<210> SEQ ID NO 15
<211> LENGTH: 372
<212> TYPE: DNA
<213> ORGANISM: Homo sapiens

<400> SEQUENCE: 15

| gacctgcttg aggtcacaca ggcagttgag agcagactga gtcttgaact tgggtctggc | 60 |
| tgatacccaa gactgtcccc actgcaatgt gacactccca gcctccagcg gaagctttgg | 120 |
| gagcaggtcc ccaaaaagcc aaagcggaag aaaaggcggc gacaaccgtg aactgcctga | 180 |
| agaacgtggt gatctggtac gaggaccaca agcaccgctg cccgtacgag ccgcacctgg | 240 |
| cgagcgtaga ccccactttt ggcctgtaca ccacggccgt gtggcagtgc gaagtggcca | 300 |
| ccgctacttc caggacctgc attcgcccct gaagcccctc agcgactcag accctgacag | 360 |
| tgacaaaggt ag | 372 |

<210> SEQ ID NO 16
<211> LENGTH: 464
<212> TYPE: DNA
<213> ORGANISM: Homo sapiens

<400> SEQUENCE: 16

| cacgggaagc cttgggagca ggtccccaaa aagccaaagc ggaagaaaag gcggcgacgc | 60 |
| aacgtgaact gcctgaagaa cgtggtgatc tggtacgagg accacaagca ccgctgcccg | 120 |
| tacgagccgc acctggcgga gctagacccc acttttggcc tgtacaccac ggccgtgtgg | 180 |
| cagtgcgaag ctggccaccg ctacttccag gacctgcatt cgcccctgaa gccccttagc | 240 |
| gactcaaaac cttgacagtg acaaagtggg caatgggctg gtggctggca gctctgactc | 300 |
| atccagctct ggctctgcct ctgactctga ggagtctcct gagggccagc cggtcaaggc | 360 |

| | |
|---|---:|
| tgcggcagcg gcagcggcag cgacacccac cagcccggtg ggcagcagcg ggctcatcac | 420 |
| tcaggagggc gtgcacattc cctttgacgt ccaccacgtg gaaa | 464 |

<210> SEQ ID NO 17
<211> LENGTH: 1956
<212> TYPE: DNA
<213> ORGANISM: Homo sapiens

<400> SEQUENCE: 17

| | |
|---|---:|
| gcggccgcca cggacggaga ctgaggctca gagggacaa gacctgcttg aggtcacaca | 60 |
| ggcagttgag agcagagctg agtcttgaac ttgggtctgg ctgatacccca agactgtccc | 120 |
| cactgcaatg tgacactccc agcctccagc ggaagccttg ggagcaggtc cccaaaaagc | 180 |
| caaagcggaa gaaaaggcgg cgacgcaacg tgaactgcct gaagaacgtg gtgatctggt | 240 |
| acgaggacca caagcaccgc tgcccgtacg agccgcacct ggcggagcta gaccccactt | 300 |
| ttggcctgta caccacggcc gtgtggcagt gcgaagctgg ccaccgctac ttccaggacc | 360 |
| tgcattcgcc cctgaagccc ctcagcgact cagaccctga cagtgacaaa gtgggcaatg | 420 |
| ggctggtggc tggcagctct gactcatcca gctctggctc tgcctctgac tctgaggagt | 480 |
| ctcctgaggg ccagccggtc aaggctgcgc cagcggcagc ggcagcgacg cccaccagcc | 540 |
| cggtgggcag cagcgggctc atcactcagg agggcgtgca cattcccttt gacgtccacc | 600 |
| acgtggaaag cctggccgag cagggtaccc cgctgtgctc caacccagca ggcaatgggc | 660 |
| ctgaagccct ggagacagtg gtgtgcgtgc cggtgcctgt gcaagtgggt gcgggcccca | 720 |
| gcgccctctt tgagaacgtg ccccaggagg ccctgggtga ggtggtggcc agctgcccca | 780 |
| tgccaggcat ggtgcccggc tcacaggtga tcatcattgc gggccctggt tacgacgctc | 840 |
| tcacggccga gggcattcac ctcaacatgg cagcaggcag cggtgtcccc ggcagtggac | 900 |
| tgggcgagga ggtgccctgt gccatgatga agggtgtggc agcctacacc agacagagc | 960 |
| ccgagggtag ccagcctagc accatggacg ccaccgcagt agcaggcatc gagaccaaga | 1020 |
| aagaaggga ggacctgtgc ttgctaaaga aggaggagaa ggaggagcca gtagccccgg | 1080 |
| agctggcaac aacggtgcct gagagcgcag agcctgaggc agaggcggac ggggaggagc | 1140 |
| tggacggcag cgacatgtca gccatcatct atgaaatccc caaggagcct gagaagaggc | 1200 |
| ggcggagcaa gcggtcgcgg gtgatggatg ctgacggcct gctcgagatg ttccactgcc | 1260 |
| catacgaggc tgcagccaa gtctacgtgg ccctcagcag cttccagaac acgtcaatc | 1320 |
| ttgtgcatcg gaaaggaaag accaaagtgt gccctcatcc tggctgtggc aagaagttct | 1380 |
| atttatccaa ccacctgcgg cggcacatga tcatccattc aggtgtccgt gaattcacct | 1440 |
| gcgagacctg cggcaagtcc ttcaagagga gaaccacct ggaggtacat cggcgcaccc | 1500 |
| acaccggcga accccctg cagtgcgaga tctgtggcta ccagtgccgg cagcgcgcgt | 1560 |
| cgctcaactg gcacatgaag aagcacactg cggaggtgca gtacaacttc acgtgcgatc | 1620 |
| gctgcgggaa gcgcttcgag aagctggaca gcgtcaagtt ccacacgctc aaaagccacc | 1680 |
| cggatcacaa gcccacctga cccacctgac cactgaccgc ccctatttat tcgtccgctc | 1740 |
| ggacaccacg cccgggcttg ccggggcctg gacagctgcg agggccgccc ggaccgcggg | 1800 |
| ccggaaggag gcgcccccgc cccgcccag agctgggccc cctgggcagg ttccccaccc | 1860 |
| cgccccaccg catccttctc ggagctggtg cctgggctg cattgctgga actgtgtcaa | 1920 |
| gagagcagag tgagattaaa gagcgagaaa ggaaaaa | 1956 |

```
<210> SEQ ID NO 18
<211> LENGTH: 66
<212> TYPE: DNA
<213> ORGANISM: Artificial Sequence
<220> FEATURE:
<223> OTHER INFORMATION: Synthetic DNA

<400> SEQUENCE: 18
ctctggtacc atgtatcctt atgatgtgcc tgattatgct tctctgatgc caggcatggt      60
gcccgg                                                                 66
```